(12) United States Patent
Okada et al.

(10) Patent No.: US 7,918,785 B2
(45) Date of Patent: Apr. 5, 2011

(54) MEDICAL APPARATUS, TREATMENT INSTRUMENT FOR ENDOSCOPE AND ENDOSCOPE APPARATUS

(75) Inventors: Tsutomu Okada, Tachikawa (JP); Yoshio Onuki, Hachioji (JP); Hiroaki Ichikawa, Hachioji (JP); Kazushi Murakami, Hino (JP); Kazuki Honda, Hachioji (JP); Yasuhito Kura, Hachioji (JP); Takaaki Komiya, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 1053 days.

(21) Appl. No.: 11/654,172

(22) Filed: Jan. 17, 2007

(65) Prior Publication Data

US 2008/0171908 A1  Jul. 17, 2008

(51) Int. Cl.
*A61B 1/00* (2006.01)
*A61B 1/04* (2006.01)

(52) U.S. Cl. ......... 600/104; 600/106; 600/128; 600/137
(58) Field of Classification Search .................. 600/104, 600/106, 137, 114, 117, 157, 155, 128, 148, 600/149
See application file for complete search history.

(56) References Cited

U.S. PATENT DOCUMENTS

| | | | | |
|---|---|---|---|---|
| 4,742,817 A | * | 5/1988 | Kawashima et al. | 600/104 |
| 4,945,920 A | | 8/1990 | Clossick | |
| 5,088,819 A | * | 2/1992 | Storz | 356/241.1 |
| 5,279,597 A | * | 1/1994 | Dassa et al. | 604/535 |
| 5,349,940 A | * | 9/1994 | Takahashi et al. | 356/241.4 |
| 5,439,478 A | | 8/1995 | Palmer | |
| 5,577,654 A | * | 11/1996 | Bishop | 227/175.1 |
| 5,620,447 A | * | 4/1997 | Smith et al. | 606/79 |
| 5,624,379 A | | 4/1997 | Ganz et al. | |
| 5,681,296 A | * | 10/1997 | Ishida | 604/523 |
| 5,954,731 A | * | 9/1999 | Yoon | 606/144 |
| 6,027,522 A | | 2/2000 | Palmer | |
| 6,440,061 B1 | * | 8/2002 | Wenner et al. | 600/114 |
| 6,656,111 B2 | * | 12/2003 | Fujii et al. | 600/146 |
| 6,743,240 B2 | * | 6/2004 | Smith et al. | 606/142 |
| 2003/0176770 A1 | * | 9/2003 | Merril et al. | 600/118 |

FOREIGN PATENT DOCUMENTS

| | | |
|---|---|---|
| DE | 196 47 761 C1 | 1/1998 |
| DE | 198 35 445 A1 | 3/1999 |
| EP | 1 362 556 A1 | 11/2003 |
| JP | 51-19390 | 2/1976 |
| JP | 2005-034623 | 2/2005 |

* cited by examiner

*Primary Examiner* — Linda C Dvorak
*Assistant Examiner* — Alireza Nia
(74) *Attorney, Agent, or Firm* — Scully, Scott, Murphy & Presser, P.C.

(57) ABSTRACT

A biopsy forceps as one of treatment instruments for endoscope includes: a tubular coil sheath introduced into a body cavity through a treatment instrument channel included in an endoscope insertion portion; a treatment portion disposed closer to a distal end side than a distal end surface of the coil sheath; an operation wire for transmitting a turning force to turn the treatment portion in a circumferential direction, the operation wire being inserted in the coil sheath in a forwardly/backwardly movable manner and turned in the circumferential direction; and a turn restricting mechanism portion for restricting a turn position of the treatment portion turned by the turning force transmitted by the operation wire with respect to the coil sheath at a first turn-restricting position or at a second turn-restricting position.

17 Claims, 16 Drawing Sheets

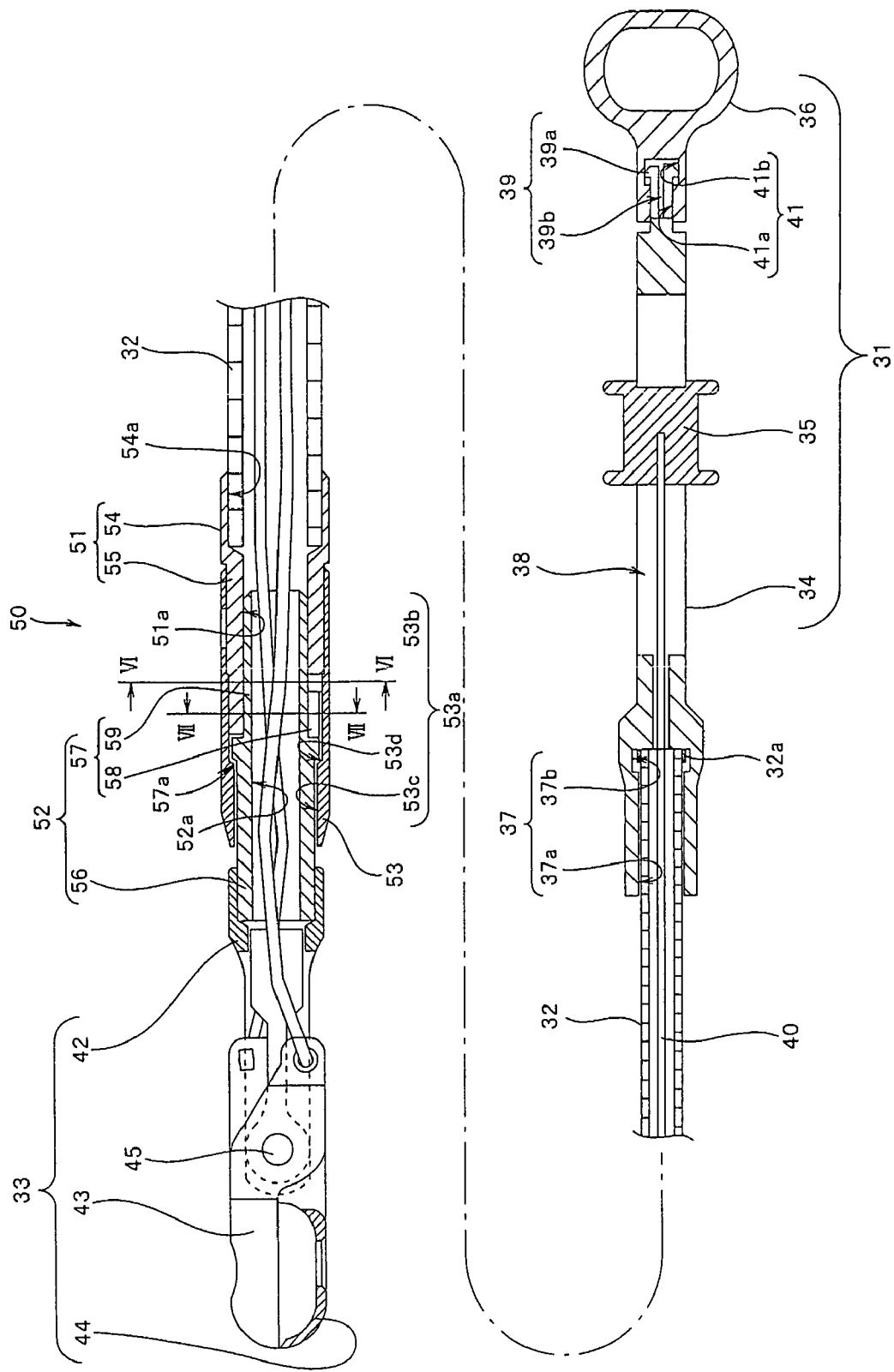

MEDICAL APPARATUS, TREATMENT INSTRUMENT FOR ENDOSCOPE AND ENDOSCOPE APPARATUS

BACKGROUND OF THE INVENTION

1. Field of the Invention

The present invention relates to a medical device capable of turning a direction of a function portion provided at a distal end of an insertion portion by a predetermined angle with respect to the insertion portion.

2. Description of Related Art

In recent years, an endoscope is widely used in the medical field. An endoscope includes an elongated insertion portion and an operation portion provided at a proximal end of the insertion portion. Generally, the elongated insertion portion has a distal end to which a bendable bending portion is provided. The operation portion is provided with, for example, a knob for operating and bending the bending portion, various switches for functioning various operations of the endoscope, a treatment instrument introducing port for inserting a treatment instrument for endoscope (hereinafter referred to as a treatment instrument) into a treatment instrument channel.

An endoscope used in the medical field includes an insertion portion which is inserted into a body cavity of a subject for observation of organs in the body cavity. Furthermore, in such an endoscope, the insertion portion is provided with a treatment instrument channel through which a treatment instrument is introduced into the body cavity, and it is possible to perform various treatments, inspections, and the like using the treatment instrument.

The treatment instrument generally includes an operation portion positioned at a hand-side, an insertion portion extended from the operation portion, and a function portion (also described as a treatment portion) provided at a distal end of the insertion portion. As such a treatment instrument, there are a treatment instrument such as an injection needle which can be used without a work for adjusting a direction of the function portion with respect to a site to be treated before a treatment, and a treatment instrument such as a biopsy forceps, a papillotomy knife, and the like, which requires a work for adjusting a direction of the function portion within a possible range with respect to the site to be treated before the treatment.

That is, when the biopsy forceps is extracted into a body cavity from the treatment instrument channel, in a case where an opening/closing direction of a biopsy cups is inconvenient with respect to a site to be treated, the direction is adjusted by turning the biopsy cups.

Methods for turning a function portion of a treatment instrument are disclosed in Japanese unexamined patent publication No. 2005-34623, U.S. Pat. No. 5,439,478, U.S. Pat. No. 6,027,522, and the like.

In the method disclosed in Japanese unexamined patent publication No. 2005-34623, the insertion tube inserted in the covering tube is turned by turning the operation portion, and the treatment portion is turned by turning the insertion tube. That is, the insertion tube is a turning force transmitting member for transmitting a turning force to turn the treatment portion.

On the other hand, in the methods disclosed in U.S. Pat. No. 5,439,478 and U.S. Pat. No. 6,027,522, the treatment portion is turnable with respect to the insertion portion, and the treatment portion is turned by turning a driving wire. That is, the driving wire is a turning force transmitting member for turning the treatment portion.

When an operator adjusts a direction of the function portion of the treatment instrument during an operation, the operator adjusts the direction by turning a turning force transmitting member located on a hand-side of the treatment instrument. The treatment instrument has flexibility so as to be able to be inserted into a treatment instrument channel provided in the elongated flexible insertion portion of the endoscope. A turning force transmitting performance of the turning force transmitting member provided to the treatment instrument is influenced by flexibility, and the turning force transmitting performance generally degrades by improving flexibility.

When the function portion provided at a distal end of the turning force transmitting member is turned by turning a hand-side of the turning force transmitting member having a poor turning force transmitting performance, in other words, having a high flexibility, twist generated in the turning force transmitting member due to the turning of the hand-side thereof is accumulated. Then the twist is released at once, so that the function portion is turned. That is, in the turning force transmitting member with poor turning force transmitting performance, the turning of the hand-side thereof is not directly transmitted to the distal end, so that it is difficult to stop the turning of the function portion in a desired direction.

Therefore, when adjusting the direction of the function portion by turning the turning force transmitting member having poor turning force transmitting performance, the operator seldom succeeds in adjusting the direction of the function portion in a desired direction by a first turning operation. The operator usually repeats the turning operation a plurality of times in order to adjust the direction of the function portion in an almost desired direction. Note that a turning force transmitting member having flexibility and rich turning force transmitting performance is expensive, and this is one reason why the treatment instrument becomes expensive.

SUMMARY OF THE INVENTION

A treatment instrument for endoscope includes: a tubular insertion portion introduced in a body cavity through a treatment instrument channel provided in an endoscope insertion portion; a treatment portion for performing a treatment in the body cavity, the treatment portion being a function portion disposed closer to a distal end side than a distal end surface of the insertion portion; a turning force transmitting member for transmitting a turning force to turn the treatment portion in a circumferential direction, the turning force transmitting member being inserted in the insertion portion in a forwardly/backwardly movable manner and turned in the circumferential direction; and a turn restricting mechanism portion for restricting a turn position of the treatment portion which is turned by the turning force transmitted by the turning force transmitting member with respect to the insertion portion at a first turn-restricting position and at a second turn-restricting position turned by a predetermined angle from the first turn-restricting position.

The above and other objects, features and advantages of the invention will become more clearly understood from the following description referring to the accompanying drawings.

BRIEF DESCRIPTION OF THE DRAWINGS

FIG. 3 is a descriptive view including a partial cross-sectional view describing a configuration of the biopsy forceps;

DETAILED DESCRIPTION OF PREFERRED EMBODIMENTS

Figure 1:
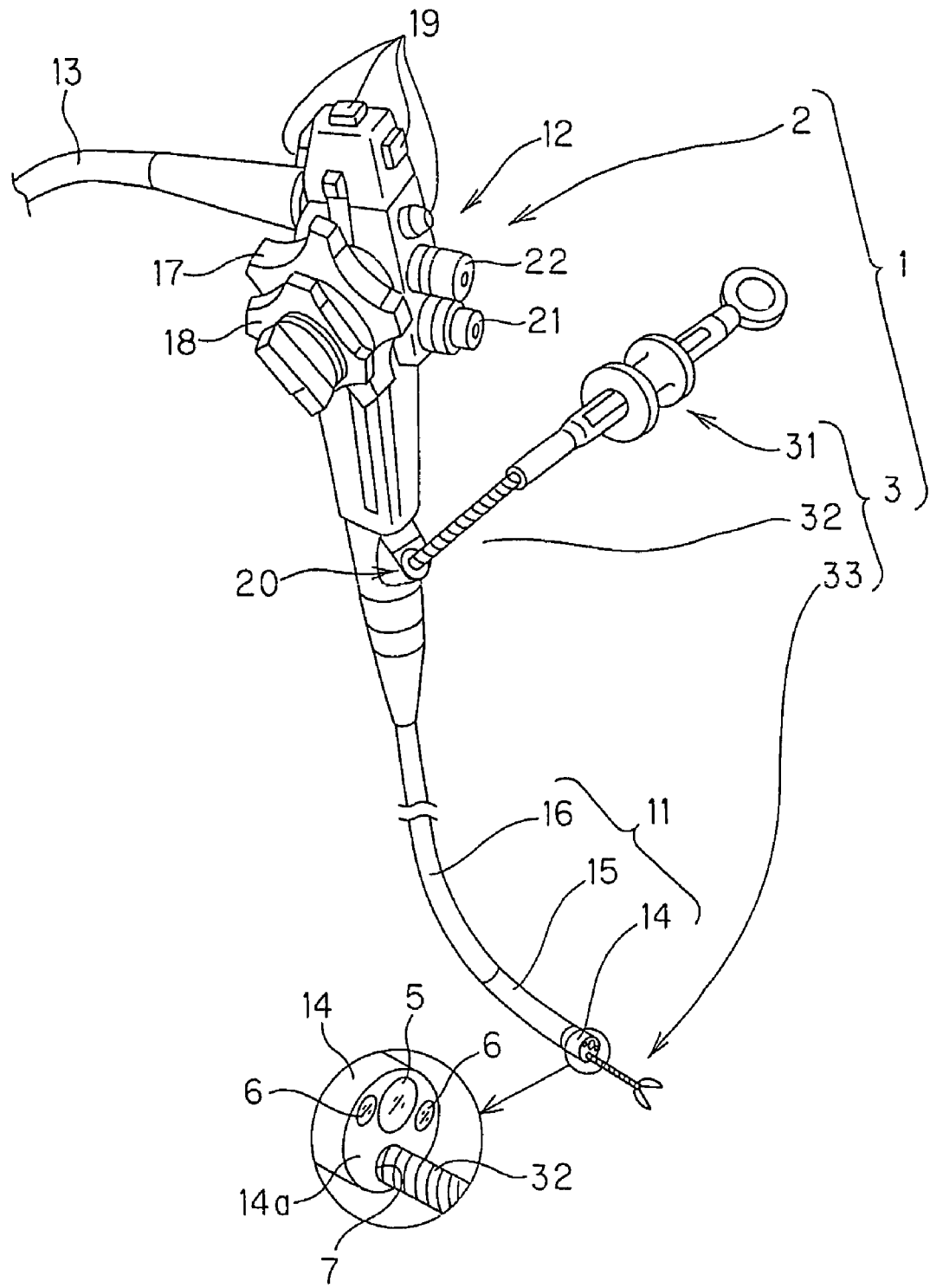
FIG. 1 is a view describing a biopsy forceps as one example of a medical device and an endoscope.

Below, an embodiment of the present invention will be described referring to the drawings.

A first embodiment of the present invention will be described referring to FIGS. 1 to 18.

As shown in FIG. 1, an endoscope apparatus 1 includes an endoscope 2, and a biopsy forceps 3 as a medical device.

The endoscope 2 includes an insertion portion 11, an operation portion 12, and a universal cord 13. The insertion portion 11 consecutively includes in the following order from a distal end side thereof, a distal end constitution portion 14, a bending portion 15, and a flexible tube portion 16. The distal end constitution portion 14 includes a distal end surface 14a on which an observation window 5, an illumination window 6, a treatment instrument extracting port 7, and the like are provided. The operation portion 12 includes an up/down bending knob 17 for bending the bending portion 15, for example, in up and down directions, a right/left bending knob 18 for bending the bending portion 15, for example, in right and left directions, and various operation switches 19. The reference numeral 20 represents a treatment instrument introducing port which communicates with the treatment instrument extracting port 7 via a treatment instrument channel. The reference numerals 21 and 22 represent an air/water feeding button and a suction button, respectively.

Meanwhile, the biopsy forceps 3 includes an operation portion 31 located on a hand side thereof, a coil sheath 32 which is an insertion portion extended from the operation portion 31, a treatment portion 33 which is a function portion, and a turn restricting mechanism portion 50. The coil sheath 32 is a densely wound coil formed by steel wire, and is formed as a flexible tube having pliability. The treatment portion 33 is provided closer to a distal end side than a distal end surface of the coil sheath 32.

Figure 2:
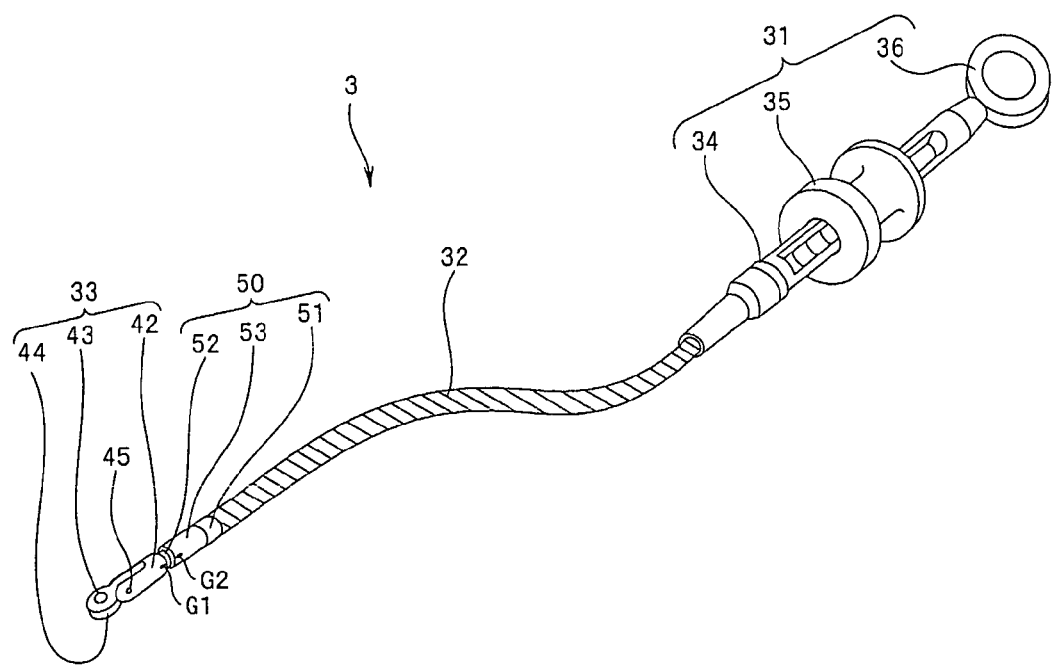
FIG. 2 is a perspective view describing the biopsy forceps.
Figure 4:
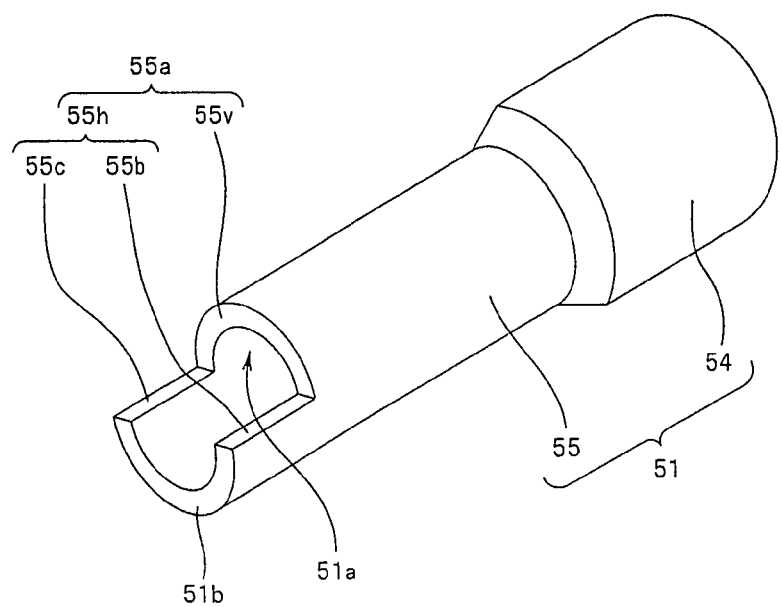
FIG. 4 is a perspective view describing a sheath fixing member.
Figure 5:
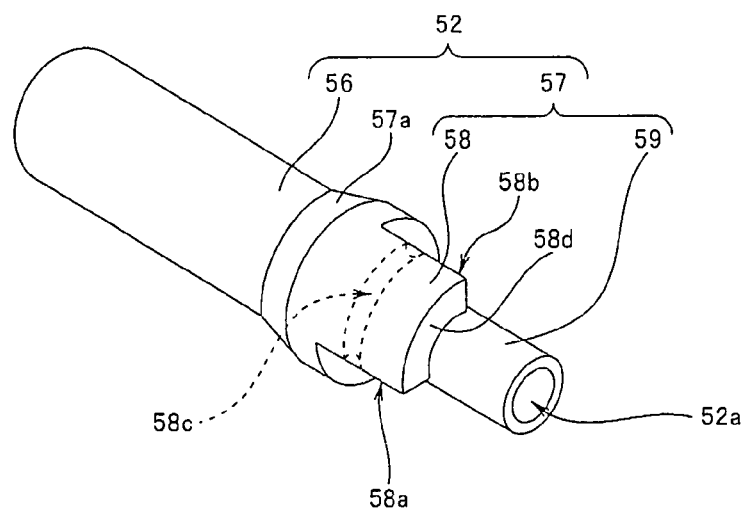
FIG. 5 is a perspective view describing a treatment portion fixing member.
Figure 6:
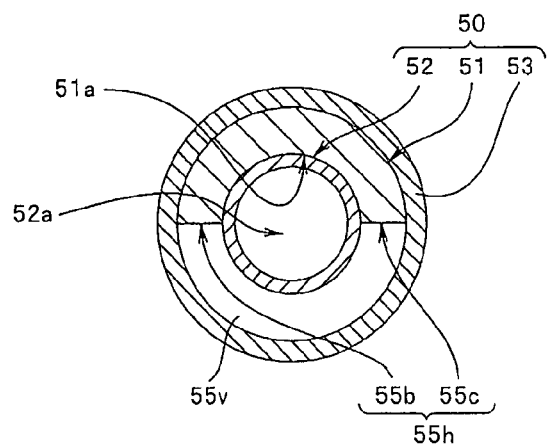
FIG. 6 is a cross-sectional view along VI-VI line of FIG. 3.

As shown in FIGS. 2 and 3, the operation portion 31 of the biopsy forceps 3 includes an operation portion main body (hereinafter abbreviated as a main body) 34, a slider 35, and a finger hooking ring 36. The main body 34 is provided with a sheath mounting portion 37, a slider disposing portion 38, and a ring mounting portion 39.

The sheath mounting portion 37 includes a hole portion 37a and a turn supporting concave portion 37b formed on a bottom surface side of the hole portion 37a. The hole portion 37a has a hole diameter larger than an outer diameter of the coil sheath 32. In the turn supporting concave portion 37b, a ring member 32a fixed to a proximal end portion of the coil sheath 32 is disposed. The turn supporting concave portion 37b has a hole diameter larger than both the hole diameter of the hole portion 37a and an outer diameter of the ring member 32a. According to such a configuration, the proximal end portion of the coil sheath 32 is turnably arranged to the sheath mounting portion 37 constituting the main body 34.

The slider 35 is slidably disposed at the slider disposing portion 38. The slider 35 includes operation wires 40 of which proximal end portions are integrally fitted thereto. The operation wires 40 are wires each made of steel, which transmit a force in a longitudinal axis direction, and are a turning force transmitting members having flexibility.

The ring mounting portion 39 is a projection portion including a flange portion 39a on an edge portion on a hand side thereof. To the ring mounting portion 39, a main body mounting portion 41 provided to the finger hooking ring 36 is mounted. The main body mounting portion 41 includes a hole portion 41a and a turn supporting concave portion 41b. The hole portion 41a has a hole diameter larger than an outer diameter of the ring mounting portion 39. The turn supporting concave portion 41b includes the flange portion 39a disposed therein. The turn supporting concave portion 41b has a hole diameter larger than both the hole diameter of the hole portion 41a and an outer diameter of the flange portion 39a. Therefore, the finger hooking ring 36 is turnable with respect to the main body 34. Note that, the ring mounting portion 39 has a slit 39b of which section is a cross-shaped, for example, and is formed to be diameter-reducible against elasticity of the ring mounting portion 39.

In the operation portion 31 according to the configuration, if the operator grasps the coil sheath 32 with one hand and turns the main body 34 with the other hand, for example, the main body 34 and the operation wires 40 integral with the slider 35 provided to the main body 34 turn with respect to the coil sheath 32.

On the other hand, the treatment portion 33 of the biopsy forceps 3 includes a treatment portion base 42, and a pair of biopsy cups (hereinafter abbreviated as cups) 43, 44. The pair of cups 43, 44 are turnably mounted at a predetermined position of the treatment portion base 42 via a pin 45. At predetermined positions of the proximal end portions of the respective cups 43, 44, distal ends of a pair of the operation wires 40 extended from the slider 35 are integrally fixed, respectively.

In the treatment portion 33 according to such a configuration, the pair of cups 43, 44 open and close with forward/backward movement of the operation wires 40. Specifically, when the slider 35 is moved forward to the distal end side with respect to the main body 34 in a state where the pair of cups 43, 44 are closed, the operation wires 40 are moved forward and the cups 43, 44 in a closed state is changed to be in an open state. On the other hand, when the slider 35 is moved backward to the hand side with respect to the main body 34 in a state where the pair of cups 43, 44 are open, the operation wires 40 are moved backward and the cups 43, 44 in the open state is changed to be in the closed state.

The turn restricting mechanism portion 50 restricts a direction of the treatment portion 33 in a first direction shown in FIG. 8 described later and a second direction shown in FIG. 9 described later. The treatment portion 33 is joined to the distal end side of the coil sheath 32 via the turn restricting mechanism portion 50.

As shown in FIG. 3, the turn restricting mechanism portion 50 includes a sheath fixing member 51, a treatment portion fixing member 52, and a joining member 53, and in the present embodiment, the direction of the treatment portion 33 can be changed from the first direction to the second direction by 90 degrees, for example. Note that, in the present embodiment, the sheath fixing member 51, the treatment portion fixing member 52, and the joining member 53 are made of metal such as stainless-steel.

The sheath fixing member 51 is a turn restricting member and is a stepped tubular member including a sheath-side central through-hole (hereinafter referred to as a proximal-end hole) 51a, as shown in FIGS. 3, 4, 6, and 7. The proximal-end hole 51a serves both as a hole in which a turning shaft portion 59 is disposed and a hole through which the operation wires 40 are inserted, which are described later. The sheath fixing member 51 includes a sheath fixing member 54 with a large diameter which constitutes a proximal end side thereof and a tubular portion 55 with a small diameter which constitutes a distal end side thereof.

The sheath fixing portion 54 has on an inner circumference thereof a sheath disposing concave portion 54a serving also as the proximal-end hole 51a. The sheath disposing concave portion 54a includes a distal end portion of the coil sheath 32 provided inside thereof. The coil sheath 32 disposed in the sheath fixing portion 54 is integrally fixed to the sheath fixing portion 54 by adhesive or soldering and the like.

The tubular portion 55 has a turn restricting portion (hereinafter abbreviated as a restricting portion) 55a formed on a distal end side thereof. The restricting portion 55a is a so-called semi-cylinder and includes a horizontally notched surface 55h formed so as to be horizontal with respect to a longitudinal axis and to include the longitudinal axis, and a vertically notched surface 55v perpendicular to the longitudinal axis. The horizontally notched surface 55h is separated into a first restricting surface 55b and a second restricting surface 55c by the proximal-end hole 51a. With the first restricting surface 55b and the second restricting surface 55c, contact surfaces 58a, 58b of a stopper portion (see reference numeral 58 of FIG. 5), described later, which is provided to the treatment portion fixing member 52 come into contact. The treatment portion fixing member 52 is a stopper member and is a stepped tubular member including a treatment portion-side central through-hole (hereinafter abbreviated as a distal-end hole) 52a, as shown in FIG. 3 and FIGS. 5 to 7. The distal-end hole 52a has the operation wires 40 inserted therethrough. The treatment portion fixing member 52 includes a treatment portion fixing portion 56 with a small diameter which constitutes a distal end side thereof and a cylinder portion 57 with a large diameter.

The treatment portion fixing portion 56 has a distal end portion to which the treatment portion base 42 constituting the treatment portion 33 is integrally fixed by a screw, a fixing pin, or by soldering, or adhesive. The treatment portion base 42 has a pair of opposing distal end-side markers G1 provided on an outer surface thereof. A boundary between the treatment portion fixing portion 56 and a cylinder portion 57 is configured as a turn holding step portion 57a.

The cylinder portion 57 includes the stopper portion 58 and the turning shaft portion 59 formed therein. The turning shaft portion 59 is formed to be a narrow tube shape by shaving the cylinder portion 57, and constitutes a proximal end side of the treatment portion fixing member 52. An outer diameter dimension and a length dimension of the turning shaft portion 59 are set so that the turning shaft portion 59 is inserted in the proximal-end hole 51a with a predetermined fit and a fitting length.

On the other hand, the stopper portion 58 is so-called a quarter cylinder, and is formed to protrude by one-quarter with respect to a whole circumference of the turning shaft portion 59 by notching the cylinder portion 57 so as to be in a quarter sector shape having 90 degrees of central angle which is formed by the contact surfaces 58a, 58b and a central axis. Note that the first contact surface 58a and the second contact surface 58b, which are in upright position with respect to the outer circumferential surface of the turning shaft portion 59 constituting the stopper portion 58, are planes parallel to the longitudinal axis.

Note that the reference numeral 58c represents a circumferential groove which is formed on an outer circumferential surface of the stopper portion 58 as shown by the dashed lines. The circumferential groove 58c is formed in a case where a click convex portion (shown by the reference numeral 53e in FIG. 14) described later is provided, and in this case, the click convex portion 53e is slidably disposed in the circumferential groove 58c.

Figure 7:
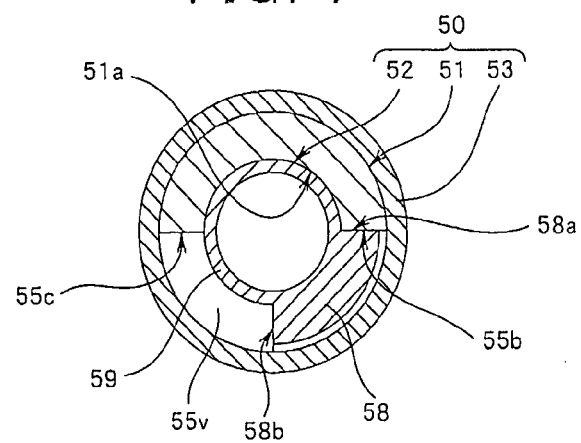
FIG. 7 is a cross-sectional view along VII-VII line of FIG. 3.

In a state where the turning shaft portion 59 of the treatment portion fixing member 52 is inserted into the proximal-end hole 51a of the sheath fixing member 51, the treatment portion fixing member 52 is disposed to be turnable by 90 degrees with respect to the sheath fixing member 51. That is, in a state where the turning shaft portion 59 is inserted into the proximal-end hole 51a, when the treatment portion fixing member 52 is turned in one direction, the first contact surface 58a comes into contact with the first restricting surface 55b as shown in FIG. 7 to be in a first restricting state, and when the treatment portion fixing member 52 is turned in the other direction, the second contact surface 58b comes into contact with the second restricting surface 55c to be in a second restricting state.

The joining member 53 has a communication hole 53a as shown in FIG. 3. The communication hole 53a is provided with a first joining member hole 53b through which the tubular portion 55 of the sheath fixing member 51, and the cylinder portion 57 including the stopper portion 58, which is included in the treatment portion fixing member 52, are inserted, and a second joining member hole 53c in which the treatment portion fixing portion 56 of the treatment portion fixing member 52 is disposed. The first joining member hole 53b has a diameter larger than that of the second joining member hole 53c, and the first joining member hole 53b and the second joining member hole 53c are concentrically formed. A bottom surface of the first joining member hole 53b is formed as a holding surface 53d for holding the turn holding step portion 57a. Therefore, in a state where the joining member 53 is disposed for the sheath fixing member 51 and the treatment portion fixing member 52, the holding surface 53d is disposed so as to face the turn holding step portion 57a of the treatment portion fixing member 52 turnably disposed with respect to the sheath fixing member 51, thereby preventing the treatment portion fixing member 52 from falling off from the sheath fixing member 51. Furthermore, the joining member 53 has a pair of opposing proximal end-side markers G2 provided on an outer surface thereof.

One example of an assembling procedure of the turn restricting mechanism portion 50 will be described.

First, a worker prepares the joining member 53 and the treatment portion fixing member 52, and inserts the treatment portion fixing portion 56 of the treatment portion fixing member 52 into the first joining member hole 53b through an opening of the first joining member hole 53b of the joining member 53. Then, the treatment portion fixing portion 56 passes through the first joining member hole 53b and the second joining member hole 53c to project from an opening of the second joining member hole 53c. Then the turn holding step portion 57a comes into contact with the holding surface 53d and the treatment portion fixing member 52 is disposed in the communication hole 53a. In this disposing state, the turning shaft portion 59 is provided in the first joining member hole 53b.

Next, the worker, in a state where the treatment portion fixing member 52 is disposed in the communication hole 53a, inserts the tubular portion 55 into the first joining member hole 53b through the opening of the first joining member hole 53b of the joining member 53. Then, the worker inserts the turning shaft portion 59 into the proximal-end hole 51a open on a distal end surface of the tubular portion 55. After that, the worker, for example, turns the sheath fixing member 51 and gradually inserts the tubular portion 55 in a deep direction, while preventing the distal end surface 51b of the tubular portion 55 from coming into contact with a distal end surface 58d of the stopper portion 58. Then, the insertion of the tubular portion 55 into the communication hole 53a is stopped by the contact of the vertically notched surface 55v with the distal end surface 58d of the stopper portion 58.

At this time, the worker confirms whether or not the treatment portion fixing member 52 turns within a range of 90 degrees turn angle, and after the confirmation, the worker integrally fixes the joining member 53 to the sheath fixing member 51 by welding and the like, for example. As a result, the turn restricting mechanism portion 50 is configured.

At this time, for example, in the first restricting state in which the first contact surface 58a of the stopper portion 58 comes into contact with the first restricting surface 55b of the horizontally notched surface 55h constituting the restricting portion 55a, the distal end-side markers G1 on the treatment portion base 42 and the proximal end-side markers G2 on the joining member 53 are fixed so as to coincide with each other.

Note that the assembly procedure of the mechanism portion 50 is not limited to the procedure described above. The turn restricting mechanism portion 50 may be configured by covering the treatment portion fixing member 52 and the sheath fixing member 51 with the joining member 53 in a state where the turning shaft portion 59 of the treatment portion fixing member 52 is disposed in advance in the proximal-end hole 51a of the sheath fixing member 51 and the vertically notched surface 55v comes into contact with the distal end surface 58d of the stopper portion 58.

The distal end portion of the sheath 32 which constitutes the biopsy forceps 3, is integrally fixed by adhesive and the like to the sheath fixing portion 54 of the sheath fixing member 51 constituting the turn restricting mechanism portion 50, as described above. On the other hand, to the distal end portion of the treatment portion fixing portion 56 of the treatment portion fixing member 52 constituting the turn restricting mechanism portion 50, the treatment portion base 42 of the treatment portion 33 is integrally fixed, as described above. Then a pair of operation wires 40, of which proximal end portions are fixed to the slider 35, are inserted through the sheath 32, the proximal-end hole 51a and the distal-end hole 52a of the turn restricting mechanism portion 50 to be extended from the treatment portion fixing member 52, and the distal ends of the operation wires 40 are integrally fixed at predetermined positions of the proximal end portions of the cups 43, 44.

Description will be made on an operation of the biopsy forceps 3 configured as described above.

Figure 8:
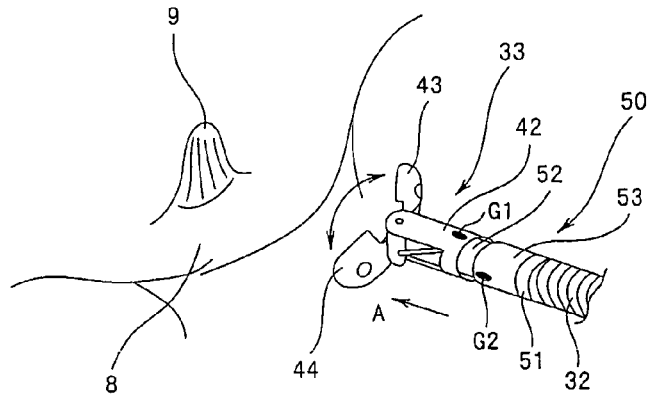
FIG. 8 is a view describing a state where a treatment portion faces a site to be treated in a first direction.
Figure 9:
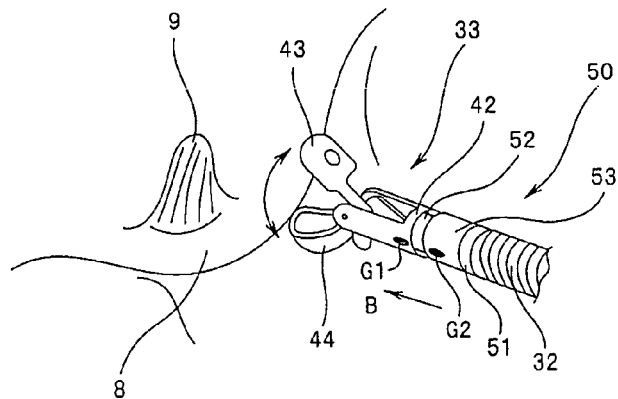
FIG. 9 is a view describing a state where the treatment portion faces the site to be treated in a second direction.

As shown in FIG. 1, an operator extracts the treatment portion 33 of the biopsy forceps 3 into a body cavity from the treatment instrument extracting port 7 of the treatment instrument channel provided to the endoscope 2, and confirms, on an endoscope screen not shown, whether the treatment portion 33 faces a site to be inspected 9 in the first direction as shown in FIG. 8, or in the second direction as shown in FIG. 9.

The facing state shown in FIG. 8 is a positional relationship in which the opening/closing direction of the cups 43, 44 of the treatment portion 33 and a height direction of the site to be inspected 9 projected from a body cavity wall (hereinafter abbreviated as a wall) 8 are crossing each other, so that the site to be inspected 9 is to be disposed between the cups 43, 44 by moving the treatment portion 33, of which cups are in the open state, closer to the site to be inspected 9 as shown by the arrow A. Therefore, the operator is capable of easily collecting the site to be inspected 9 with the treatment portion 33 by performing an operation of closing the cups 43, 44.

On the other hand, the facing state shown in FIG. 9 is a positional relationship in which the opening/closing direction of the cups 43, 44 of the treatment portion 33 almost coincides with the height direction of the site to be inspected 9. Therefore, when the treatment portion 33, of which cups are in the open state, is moved closer to the site to be inspected as shown by the arrow B, the cup 44 located on a side of the wall 8 is disposed on a root side of the site to be inspected 9. In this positional relationship, even if the cups 43, 44 are closed, only a part of the site to be inspected 9 can be collected by the treatment portion 33, so that sufficient collection is difficult as described above.

In the biopsy forceps 3 according to the present invention, when the treatment portion 33 is extracted into a body cavity from the treatment instrument extracting port 7 of the treatment instrument channel provided to the endoscope 2, in a case where the treatment portion 33 faces the site to be inspected 9 in the second direction as shown in FIG. 9, the operator performs an operation of changing the direction of the treatment portion 33 by 90 degrees in view of workability, and changes the positional relationship such that the treatment portion 33 faces the site to be inspected 9 in the first direction shown in FIG. 8.

Now, description will be made on the operation of changing the direction of the treatment portion 33.

First, the operator opens the cups 43, 44, to confirm the facing state thereof. If the facing state is different from a desired one, the operator grasps the coil sheath 32 of the biopsy forceps 3 with one hand in order to change the direction of the treatment portion 33, and turns the main body 34 in a predetermined direction with the other hand. Then, with the turn of the main body 34, the slider 35 disposed at the slider disposing portion 38 of the main body 34 is turned, and the operation wires 40 of which proximal end portions are integrally provided to the slider 35 are turned with respect to the coil sheath 32. However, the coil sheath 32 is an elongated flexible member, so that the direction of the treatment portion 33 is not changed by the turn of the main body 34, and the operation wires 40 are twisted.

If the operator continues turning the main body 34, the operation wires 40 are further twisted, and the twisting force is accumulated in the operation wires 40. Then, when the twisting force accumulated in the operation wires 40 exceeds a, predetermined amount, the twisting force accumulated in the operation wires 40 is released at once. That is, the turn of the main body 34 is transmitted to the distal ends of the operation wires 40, and the treatment portion 33 is turned to face the site to be inspected 9 in the first direction shown in FIG. 8.

This is because, as described in FIG. 3 and the like, the cups 43, 44, to which the distal ends of each of the operation wires 40 are fastened respectively, are mounted to the treatment portion base 42, and the proximal end portion of the treatment portion base 42 is integrally fixed to the treatment portion fixing portion 56 of the treatment portion fixing member 52 turnably disposed to the turn restricting mechanism portion 50.

Figure 10:
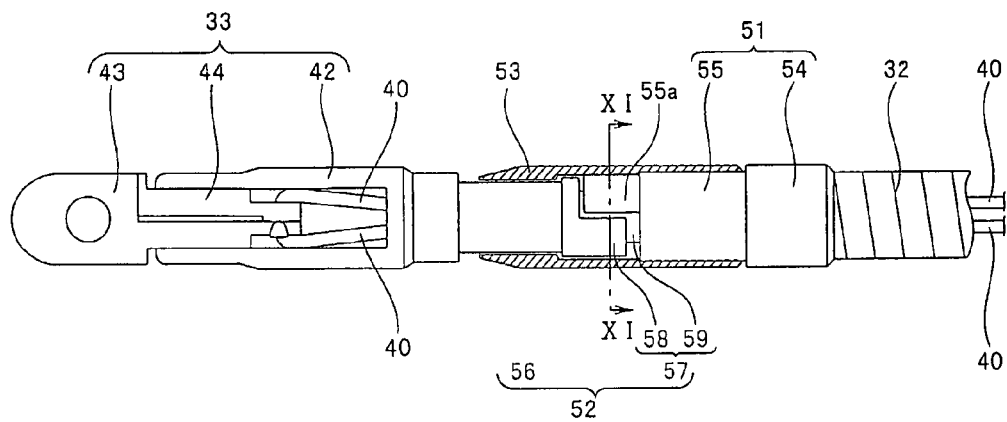
FIG. 10 is a view describing a relationship between a stopper portion and a turn restricting portion when the treatment portion faces the first direction.
Figure 11:
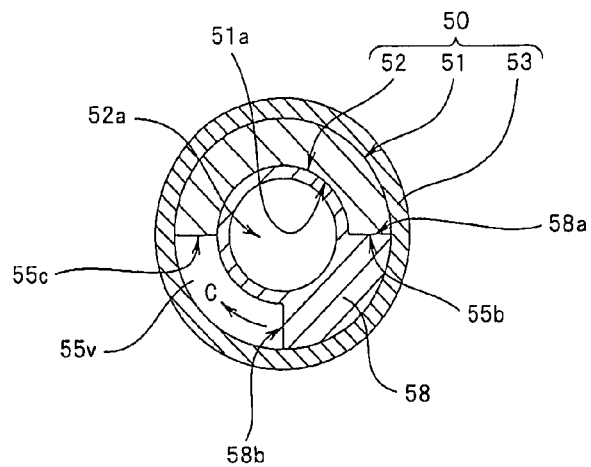
FIG. 11 is a cross-sectional view along XI-XI line of FIG. 10.

Therefore, when the treatment portion 33 faces the site to be inspected 9 as shown in FIG. 9, a positional relationship between the restricting portion 55a and the stopper portion 58 constituting the turn restricting mechanism portion 50 is a relationship as shown in FIGS. 10 and 11. That is, the relationship is the first restricting state in which the first contact surface 58a of the stopper portion 58 comes into contact with the first restricting surface 55b of the horizontally notched surface 55h constituting the restricting portion 55a.

At this time, the distal end-side markers G1 on the treatment portion base 42 and the proximal end-side markers G2 on the joining member 53 coincide with each other.

Figure 12:
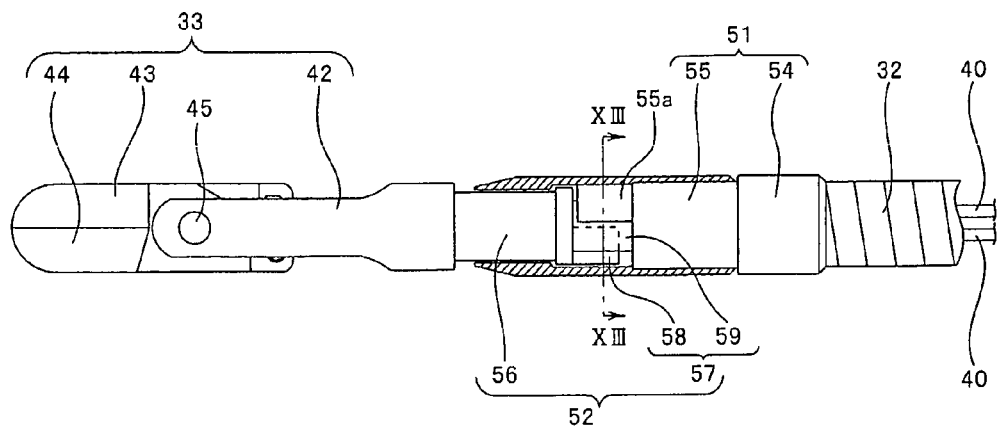
FIG. 12 is a view describing a relationship between the stopper portion and the turn restricting portion when the treatment portion faces the second direction.
Figure 13:
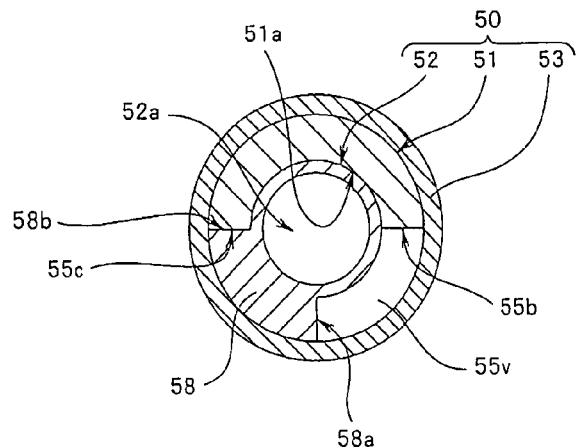
FIG. 13 is a cross-sectional view along XIII-XIII line of FIG. 12.

When the twisting force accumulated in the operation wires 40 is released at once in the first restricting state in which the first contact surface 58a comes into contact with the first restricting surface 55b, the turn of the main body 34 is transmitted to the distal ends of the operation wires 40, so that the treatment portion 33 is turned. Then, the stopper portion 58 of the turn restricting mechanism portion 50 is turned in the direction of the arrow C by the turn of the treatment portion 33, and after being turned and moved by 90 degrees, as shown in FIGS. 12, 13, the turn restricting mechanism portion 50 becomes the second restricting state in which the second contact surface 58b of the stopper portion 58 comes into contact with the second restricting surface 55c of the horizontally notched surface 55h constituting the restricting portion 55a, and the turn of the treatment portion 33 is stopped. At this time, the treatment portion 33 faces the site to be inspected 9 in the first direction as shown in FIG. 8, after being turned by 90 degrees from the position in the state of facing the site to be inspected 9 in the direction as shown in FIG. 9. The positions of the distal end-side markers G1 on the treatment portion base 42 and the proximal end-side markers G2 on the joining member 53 are shifted by 90 degrees each other.

After this, the operator moves the treatment portion 33, of which cups 43, 44 are in the open state, closer to the site to be inspected 9 as shown by the arrow A, so that the site to be inspected 9 is disposed between the cups 43, 44. Therefore, the operator can put the site to be inspected 9 in the cups 43, 44 by performing the operation of closing the cups 43, 44.

As described above, in the present embodiment, the operator can change the direction of the treatment portion 33 by 90 degrees. When changing the direction of the treatment portion, the operator turns the main body 34 to accumulate the twisting force in the operation wires 40. When the twisting force accumulated in the operation wires 40 exceeds a predetermined amount, the force is released at once to turn the treatment portion 33. When the treatment portion 33 is turned, the turn of the treatment portion 33 is transmitted to the treatment portion fixing portion 56 via the treatment portion base 42, and thereby the treatment portion fixing member 52 is turned. Then, when the stopper portion 58 provided to the treatment portion fixing member 52 is turned by 90 degrees, the turn restricting mechanism portion becomes the first restricting state in which the first contact surface 58a of the stopper portion 58 comes into contact with the first restricting surface 55b of the restricting portion 55a or the second restricting state in which the second contact surface 58b comes into contact with the second restricting surface 55c. That is, the direction of the treatment portion 33 is changed only by 90 degrees by the twisting force accumulated in the operation wires 40 to be released at once.

In this way, the turn restricting mechanism portion capable of changing between the first restricting state and the second restricting state by the contact of the stopper portion and the restricting portion is provided in the vicinity of the treatment portion away from the operation portion main body. As a result, when the treatment portion is turned due to the release of the twisting force accumulated in the operation wires 40 with the turning operation of the operation portion main body, the contact surface comes into contact with the restricting surface, and thereby the treatment portion can be stopped after being turned by 90 degrees.

Furthermore, in the first restricting state or in the second restricting state, the distal end-side markers G1 on the treatment portion base 42 and the proximal end-side markers G2 on the joining member 53 are coincided with each other, so that a turnable direction can be confirmed based on the state of the markers. That is, for example, if the markers G1 and G2 are coincided with each other in the first restricting state as shown in FIGS. 10, 11, the turnable direction is counterclockwise. Therefore, if the markers G1 and G2 are shifted each other, it is possible to determine that the turnable direction is clockwise.

According to this, by using an inexpensive operation wire which is poor in turning force transmitting performance but excellent in flexibility, it is possible to obtain the biopsy forceps capable of changing the direction of the treatment portion between the first direction and the second direction with reduced cost.

Figure 14:
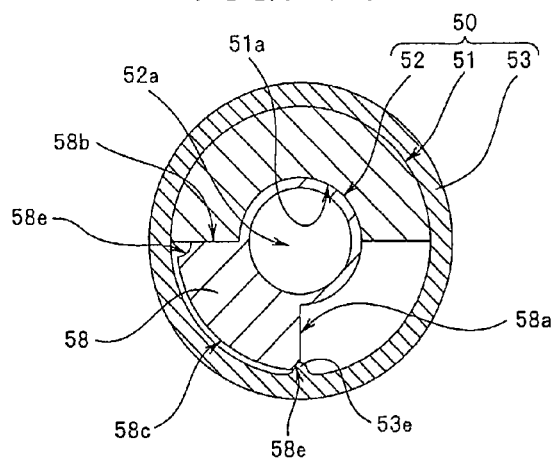
FIG. 14 is a view describing a configuration and an operation of a joining member provided with a click portion.

Note that the turn restricting mechanism portion 50 shown in FIG. 14 has the semispherical click convex portion 53*e* provided at a predetermined position on an inner circumferential surface of the joining member 53. On the other hand, to the stopper portion 58, provided is the circumferential groove 58*c* having a semicircular cross section in which the click convex portion 53*e* is engaged and disposed. On the sides of the contact surfaces which are the both end sides of the circumferential groove 58*c*, provided are the concave portions 58*e* in which the click convex portion 53*e* is engaged and disposed. The click convex portion 53*e* has a radius formed to be larger than that of the circumferential groove 58*c* by a predetermined dimension. Furthermore, the concave portions 58*e* are so formed as to be larger than the radius of the click convex portion 53*e*.

According to the configuration, it is possible to stably obtain the first restricting state or the second restricting state of the turn restricting mechanism portion 50 by engaging and disposing the click convex portion 53*e* in the concave portion 58*e* on the side of the first contact surface 58*a* or in the concave portion 58*e* on the side of the second contact surface 58*b*.

However, by providing the click convex portion 53*e* and the concave portions 58*e*, more twisting force is required in changing the direction of the treatment portion 33.

Figure 15:
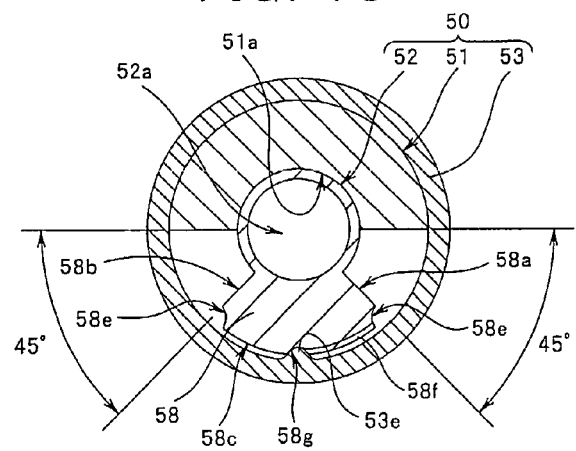
FIG. 15 is a view describing another configuration and an operation of the joining member provided with the click portion.

Furthermore, in the turn restricting mechanism portion 50 shown in FIG. 15, in addition to the concave portions 58*e* provided on the both end portions of the circumferential groove 58*c*, a middle concave portion 58*g* in which the click convex portion 53*e* is engaged and disposed is provided at a position which is a mid-way part of the circumferential groove 58*c*, for example at a position dividing an arc 58*f* into half. The disposing position of the stopper portion 58 when the click convex portion 53*e* is engaged in the middle concave portion 58*g* is assumed to be a disposing position at the time of insertion.

According to the configuration, the biopsy forceps 3 is extracted into the body cavity through the treatment instrument channel provided to the endoscope 2, with the click convex portion 53*e* being disposed in advance in the middle concave portion 58*g* of the stopper portion 58. In this case, when the treatment portion 33 and the site to be inspected 9 are in the facing state as shown in FIG. 8, without the operation of changing the direction of the treatment portion, it is possible to dispose the site to be inspected 9 between the cups 43, 44 by moving the treatment portion 33 closer to the site to be inspected 9 with the cups being open, as shown by the arrow A in FIG. 8.

On the other hand, when the treatment portion 33 of the biopsy forceps 3 is extracted into the body cavity from the treatment instrument extracting port 7, in a case where the positional relationship between the treatment portion 33 and the site to be inspected 9 is different from a desired one, the operation of changing the direction of the treatment portion 33 by 45 degrees is performed first in the configuration according to the present embodiment. Specifically, the operator is capable of making the treatment portion 33 face the site to be inspected 9 as shown in FIG. 8 by selectively turning the main body 34 clockwise or counterclockwise.

This makes it possible to easily set the positional relationship between the treatment portion 33 extracted into the body cavity through the treatment instrument channel and the site to be inspected 9 in the first direction shown in FIG. 8.

In the above-described embodiment, the middle concave portion 58*g* is provided at the position dividing the arc 58*f* into half. However, the position where the middle concave portion 58*g* is provided is not limited to the position dividing the arc 58*f* into half, and may be another position.

Moreover, the above-described embodiment shows a configuration in which the turn restricting mechanism portion 50 is provided close to the treatment portion 33. However, the position where the turn restricting mechanism portion 50 is provided may be a position away from the treatment portion 33 by several centimeters, and in that case, a biopsy forceps 3A is configured as shown in FIG. 16.

Figure 16:
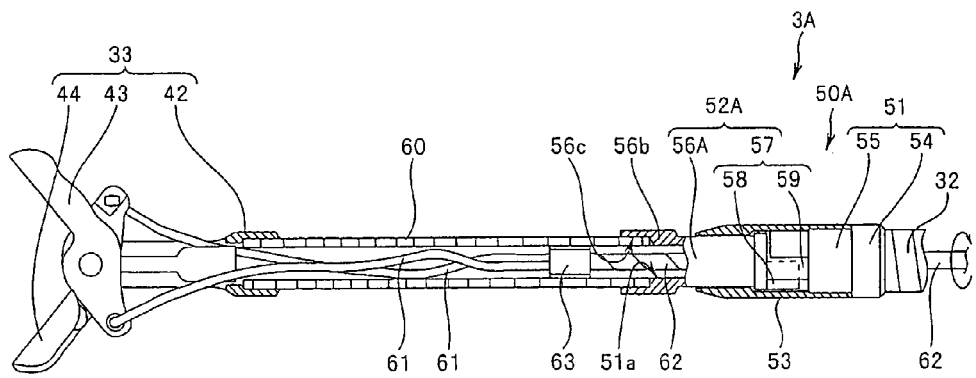
FIG. 16 is a view describing a configuration of a biopsy forceps provided with a connecting member for connecting a pair of cups and a turn restricting mechanism portion.

In the biopsy forceps 3A shown in FIG. 16, the treatment portion 33 is joined to the distal end side of the coil sheath 32 through a short coil 60 which is a connecting member and a turn restricting mechanism portion 50A. To a distal end portion of the short coil 60, the treatment portion base 42 constituting the treatment portion 33 is integrally fixed similarly as in the first embodiment. To a proximal end portion of the short coil 60, a distal end portion of a treatment portion fixing member 52A constituting the turn restricting mechanism portion 50A is integrally fixed. At a distal end side of a treatment portion fixing portion 56A constituting the treatment portion fixing member 52A, a coil fixing portion 56*b* is provided. The coil fixing portion 56*b* has a coil disposing concave portion 56*c* at an inner circumference thereof, and in the coil disposing concave portion 56*c*, the proximal end portion of the short coil 60 is disposed. The short coil 60 is integrally fixed to the coil fixing portion 56*b* by adhesive or soldering and the like.

In the present embodiment, the turning force transmitting member includes a pair of first operation wires 61, a single second operation wire 62, and a wire joining member 63. The respective distal end portions of the pair of the first operation wires 61 are integrally fixed at predetermined positions of the proximal end portions of the cups 43, 44. On the other hand, the respective proximal end portions of the pair of the first operation wires 61 are integrally fixed to a distal end portion of the second operation wire 62 through the wire joining member 63.

That is, in the present embodiment, the pair of first operation wires 61, the distal end side of the second operation wire 62, and the wire joining member 63 are movably disposed in the short coil 60. The second operation wire 62 extended from the short coil 60 is inserted through the proximal-end hole 51*a* included in the turn restricting mechanism portion 50A, a distal-end hole not shown, and the coil sheath 32, to be fixed to the slider 35.

According to the configuration, the operation wire inserted in the coil sheath is one piece of wire, so that a part where the inner circumferential surface of the coil sheath and the operation wire contact each other is reduced, thereby improving an operability of forward and backward movements of the operation wire.

Furthermore, in the above-described embodiment, the first restricting surface 55*b* and the second restricting surface 55*c* are provided on the horizontally notched surface 55*h* of the restricting portion 55a, while the first contact surface 58a and the second contact surface 58b are provided such that the central angle of the stopper portion 58 is formed to be 90 degrees, thereby obtaining the 90 degrees of turn angle. However, the turn angle is not limited to 90 degrees as long as the angle is not exceeding 180 degrees. In addition, also in setting the 90 degrees of turn angle, for example, the configuration is not limited to one in which the central angle of the restricting portion is formed to be 180 degrees while the central angle of the stopper portion is formed to be 90 degrees. For example, the 90 degrees of turn angle may be obtained such that the central angle of the restricting portion is formed to be 120 degrees and the central angle of the stopper portion is formed to be 30 degrees. That is, a desired turn angle may be obtained by appropriately setting the central angles of the restricting portion and the stopper portion.

Figure 17:
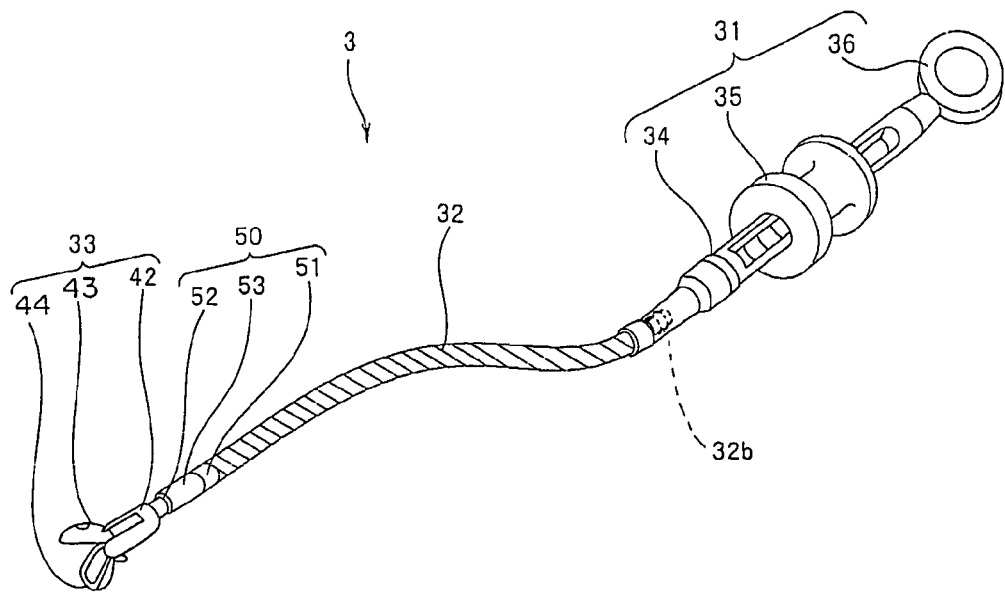
FIG. 17 is a view describing a biopsy forceps having a main body to which a screw provided at a proximal end portion of a coil sheath is screwed.
Figure 18:
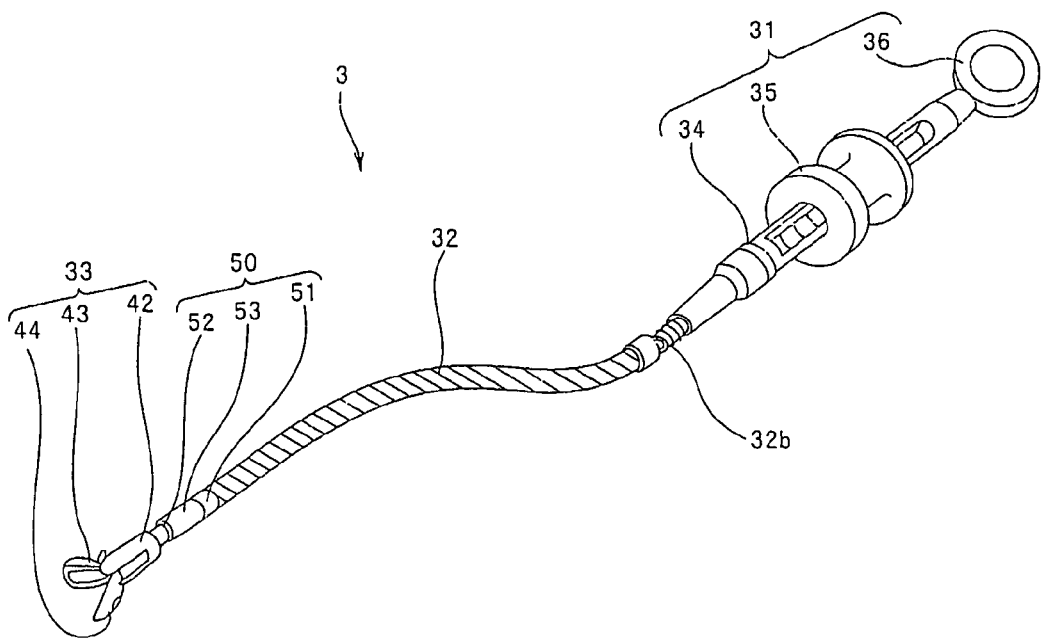
FIG. 18 is a view describing a biopsy forceps having the main body from which the screw provided at the proximal end portion of the coil sheath is exposed.

Furthermore, indications for recognizing a turnable direction may be configured as shown in FIGS. 17 and 18. That is, a screw 32b is provided at the proximal end of the coil sheath 32 and is screwed to the main body 34. For example, in the first restricting state as shown in FIG. 7, the screw 32b is screwed to the main body 34 as shown in FIG. 17, and the restricting state can be changed to the second restricting state by turning the main body 34 counterclockwise. At this time, the screw 32b slackens to be exposed from the main body as shown in FIG. 18, so that the operator recognizes the restricting state is the second restricting state, and in the state, the operator can determine that turn in the clockwise direction in which the screw 32b screws to the main body 34 is possible.

A second embodiment of the present invention will be described referring to FIGS. 19 and 20.

In the second embodiment, the medical device is a grasping forceps 70 provided with a turn restricting mechanism portion 50B and configured such that a direction of a treatment portion 33A of the grasping forceps 70 is changed by 120 degrees by operating an operation portion not shown.

Figure 19:
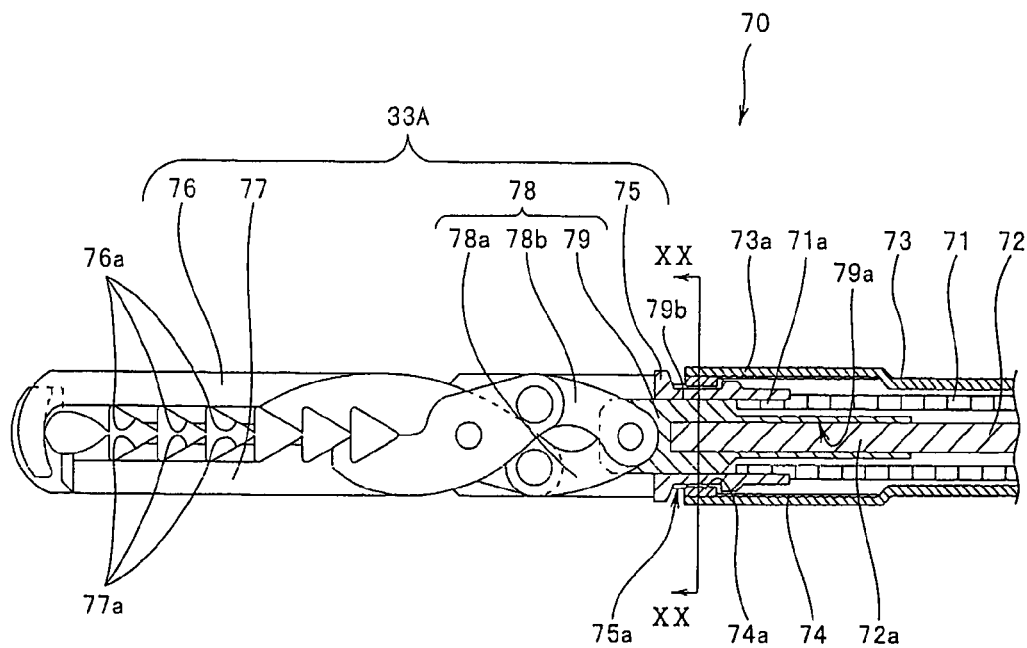
FIG. 19 is a view describing a treatment portion of a grasping forceps.
Figure 20:
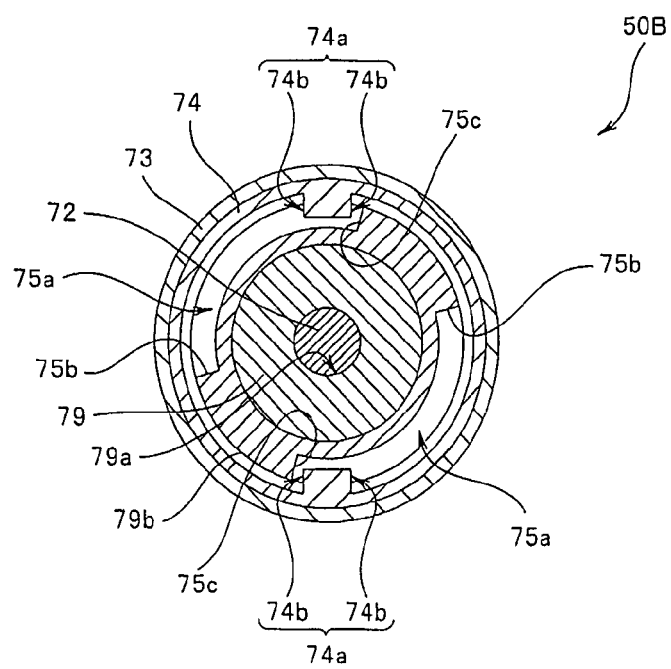
FIG. 20 is a cross-sectional view along XX-XX line of FIG. 19.

The grasping forceps 70 according to the present embodiment is provided with a coil sheath 71 as shown in FIG. 19. The coil sheath 71 has a distal end 71a to which a distal end cover 75 as a stopper member, described later, constituting the treatment portion 33A is provided in a fixed manner, and a proximal end integrally fixed to a main body of the operation portion not shown.

The treatment portion 33A includes the distal end cover 75, a pair of openable/closable forceps pieces 76, 77 opposing to each other which are connected to a distal end of the distal end cover 75, and a link mechanism portion 78 for converting a forward/backward movement operation of an operation wire 72 to an opening/closing operation of the pair of the forceps pieces 76, 77. Each of the pair of forceps pieces 76, 77 is formed by a generally bar-like metal piece extended from a proximal end to a distal end. Opposing surfaces 76a, 77a of the forceps pieces 76, 77 are grasping surfaces for grasping an affected part and formed to have a corrugated shape.

The link mechanism portion 78 includes a connecting member 79, a pair of relay members 78a, 78b. The connecting member 79 has a stepped cylinder shape and includes a wire hole 79a in which a distal end portion 72a of the operation wire 72 is disposed to be integrally fixed by adhesive, soldering, or welding and the like. The forceps piece 76 and the connecting member 79 are connected via the relay member 78a. The forceps piece 77 and the connecting member 79 are connected via the relay member 78b.

The distal end cover 75 is formed to have a circular tube shape, and on an inner circumferential surface of a proximal end portion thereof, the sheath distal end 71a of the coil sheath 71 is integrally fixed. On the other hand, on an outer circumferential surface of a proximal end portion of the distal end cover 75, circumferential concave portions 75a in which a pair of turn restricting convex portions 74a described later are disposed and engaged, respectively. Each of the circumferential concave portions 75a constitutes a first contact surface 75b and a second contact surface 75c.

An outer circumferential surface side of the coil sheath 71 is covered with a covering tube 73 constituting the insertion portion. The covering tube 73 has electrical insulating properties and is made of a pliable resin. A tube distal end 73a has an inner hole to which a tubular turn restricting member 74 is provided in a fixed manner. The turn restricting member 74 has at a distal end portion thereof the pair of turn restricting convex portions 74a protruding from an inner circumferential surface in a central direction, which are provided in a positional relationship opposing to each other, as shown in FIG. 20. Each of the turn restricting convex portions 74a is provided with a first restricting surface 74b and a second restricting surface 74c.

The turn restricting convex portions 74a of the turn restricting member 74 are engaged in the circumferential concave portions 75a of the distal end cover 75, and thereby the covering tube 73 to which the turn restricting member 74 is provided in a fixed manner and the distal end cover 75 are joined. In the joining state, the distal end cover 75 is turnable with respect to the turn restricting member 74, while forward/backward movement thereof in a longitudinal axis direction is restrained. In the present embodiment, the turn restricting mechanism portion 50B includes the distal end cover 75 provided with the circumferential concave portions 75a and the turn restricting member 74 provided with the turn restricting convex portions 74a.

Then, the treatment portion 33A configured as described above is opened and closed with the forward/backward movement operation of the operation wire 72 inserted into the coil sheath 71, and is turned by turning the coil sheath 71 and the operation wire 72.

In the turn restricting mechanism portion 50B of the present embodiment, the distal end cover 75 is configured to turn from a position of a first restricting state in which the first contact surfaces 75b of the pair of the circumferential concave portions 75a and the first restricting surfaces 74b of the turn restricting convex portions 74 come into contact with each other to a position of a second restricting state in which the second contact surfaces 75c of the of the circumferential concave portions 75a and the second restricting surfaces 74c of the turn restricting convex portions 74a come into contact with each other. The turn angle is set to be 120 degrees, for example.

Description will be made on an operation of the grasping forceps 70 provided with the turn restricting mechanism portion 50B configured as described above.

The treatment portion 33A of the grasping forceps 70 is extracted into a body cavity from the treatment instrument extracting port 7 of the treatment instrument channel provided to the endoscope 2 to be faced with an affected part to be grasped (not shown), and it is confirmed whether or not an opening/closing direction of the pair of the forceps pieces 76, 77 and a direction of the affected part coincide with each other on an endoscope screen not shown.

At this time, in a case where the treatment portion 33A faces the affected part in a desired direction, the operator moves on to a procedure for grasping the affected part. On the other hand, in a case where the treatment portion 33A does not face the affected part in the desired direction, the operator performs an operation of changing the direction of the treatment portion 33A. That is, the operator performs an operation of turning the operation portion not shown to turn the coil sheath 71 and the operation wire 72 with respect to the covering tube 73.

Note that, the covering tube 73 is in a state generally fixed to the treatment instrument channel due to a high friction with the treatment instrument channel, so that the covering tube 73 does not turn with the turn of the coil sheath 71.

The coil sheath 71 and the operation wire 72 are twisted with a turning operation of the operation portion, and a twisting force is gradually accumulated in the coil sheath 71 and the operation wire 72 due to a continuation of turning operation of the operation portion by the operator. Then, when the twisting force accumulated in the coil sheath 71 and the operation wire 72 exceeds a predetermined amount, the twisting force accumulated in the coil sheath 71 and the operation wire 72 is released at once. This allows the hand-side turning operation to be transmitted to the distal ends of the coil sheath 71 and the operation wire 72, and thereby the treatment portion 33A as well as the distal end cover 75 is turned.

Then, due to the turn of the distal end cover 75, the turn restricting mechanism portion 50B changes from the first restricting state in which the first contact surfaces 75b of the circumferential concave portions 75a and the first restricting surfaces 74b of the turn restricting convex portions 74a come into contact with each other to the second restricting state in which the second contact surfaces 75c of the circumferential concave portions 75a and the second restricting surfaces 74c of the turn restricting convex portions 74a come into contact with each other. That is, the direction of the treatment portion 33A with respect to the affected part is turned by 120 degrees, so that the opening/closing direction of the pair of the forceps pieces 76, 77 almost coincide with the direction of the affected part.

After that, the operator moves on to the procedure for grasping the affected part, in which the operator operates and moves forwardly/backwardly the operation wire 72 to open and close the pair of the forceps pieces 76, 77, thereby grasping the affected part.

The turn restricting mechanism portion which is capable of changing between the first restricting state and the second restricting state by the contact of connecting member and the turn restricting member is thus provided in the vicinity of the treatment portion away from the operation portion main body. Therefore, when the treatment portion is turned due to the release of twisting force accumulated in the coil sheath and the operation wire with the turning operation of the operation portion, the treatment portion is stopped after being turned by 120 degrees, by the contact of the contact surface and the restricting surface.

Note that the turn angle is 120 degrees in the present embodiment, but the turn angle is not limited to 120 degrees. It is possible to obtain a desired turn angle by appropriately setting the circumferential concave portions and the turn restricting convex portions.

A third embodiment of the present invention will be described referring to FIGS. 21 to 26.

In the third embodiment, the medical device is a papillotomy knife 80 as a kind of a high-frequency treatment instrument, which is provided with a turn restricting mechanism portion 50C. A direction of a dissection portion 33B which is a function portion of the papillotomy knife 80 is configured to be changed by 30 degrees in counterclockwise direction under a manual operation of an operation portion not shown.

The papillotomy knife 80 according to the present embodiment mainly includes a tubular flexible outer sheath 81 and an annular rigid turn restricting member 82 which constitute an elongated flexible insertion portion extended from the operation portion not shown; a tubular flexible inner sheath 83 as a turning force transmitting member which is inserted in the outer sheath 81, a conductive wire 84 inserted in the inner sheath 83, and a generally annular stopper member 85 disposed at a predetermined position of a distal end portion of the inner sheath 83.

Note that, in the present embodiment, the outer sheath 81 and the turn restricting member 82 are made of an insulating member, or outer circumferential surfaces thereof are coated by an insulating member. In addition, a blade 86 is coated on an outer circumference of the inner sheath 83 for the purpose of improving a turn-following capability.

Wire extracting ports 83b are formed at two positions, that is, at front and rear positions on an inner sheath distal end 83a of the inner sheath 83. A wire distal end 84a of the conductive wire 84 inserted in the inner sheath distal end 83a is extracted outside of the inner sheath 83 from these wire extracting ports 83b. An exposing portion of the wire distal end 84a exposed outside of the inner sheath 83 is configured as the dissection portion 33B, a so-called knife portion 83c.

To the operation portion not shown positioned on the hand side, a linear-shaped guide member and a slider which slides along the guide member, for example, are provided. To the guide member, a proximal end portion of the inner sheath 83 is provided in a fixed manner. The inner sheath 83 is configured to turn with respect to the outer sheath 81 by turning the guide member.

On the other hand, to the slider, a proximal end portion of the conductive wire 84 is joined. The conductive wire 84 is moved forward/backward with a forward/backward movement operation of the slider, and the knife portion 83c is operated to be pushed and pulled by the forward/backward movement of the conductive wire 84.

Specifically, when the operator pulls the slider to the hand side, the inner sheath distal end 84a of the inner sheath 83 is bent in an arched line, thereby forming the knife portion 83c in a bowstring shape, not shown. On the other hand, when the operator pushes the slider to the distal end side, the knife portion 83c in a circular arc shape, not shown, is formed. Then, in a state where the bowstring-shaped or the circular arc-shaped knife portion 83c is formed, a high frequency current is energized to the conductive wire 84, thereby allowing dissection of a living tissue.

Figure 21:
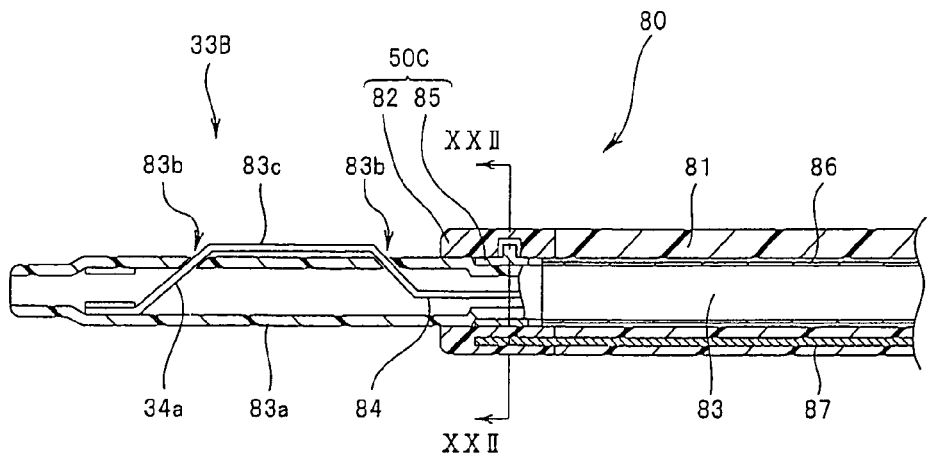
FIG. 21 is a view describing a configuration of a papillotomy knife.
Figure 22:
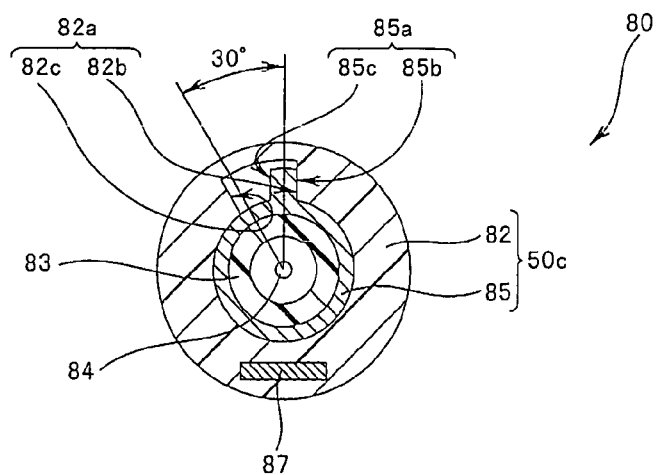
FIG. 22 is a cross-sectional view along XXII-XXII line of FIG. 21.
Figure 25:
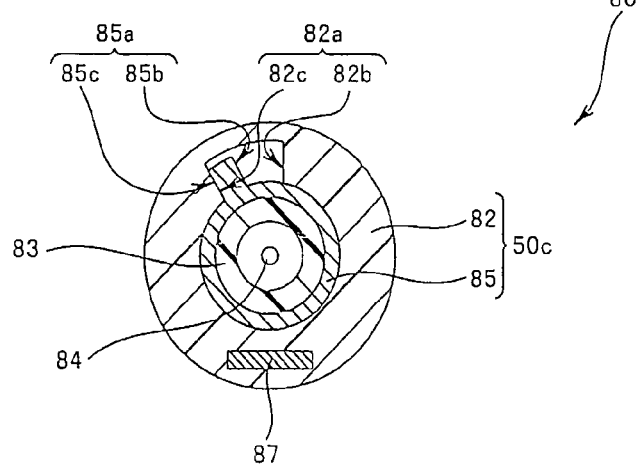
FIG. 25 is a view describing the papillotomy knife when the turn restricting mechanism portion is in a second restricting state.

In the present embodiment, the turn restricting mechanism portion 50C includes the turn restricting member 82 and the stopper member 85. As shown in FIGS. 21, 22, and 25, the turn restricting member 82 includes a circumferential concave portion 82a having a first restricting surface 82b and a second restricting surface 82c. On the other hand, the stopper member 85 includes a stopper portion 85a having a first contact surface 85b and a second contact surface 85c, which is provided in a projecting manner. Then, the stopper portion 85a of the stopper member 85 is disposed so as to engage in the circumferential concave portion 82a of the turn restricting member 82, and as a result, the turn restricting mechanism portion 50C is configured.

In the turn restricting mechanism portion 50C of the present embodiment, the stopper portion 85a is turnable from a position in a first restricting state in which the first contact surface 85b of the stopper portion 85a comes into contact with the first restricting surface 82b of the circumferential concave portion 82a to a position in a second restricting state in which the second contact surface 85c of the stopper portion 85a comes into contact with the second restricting surface 82c of the circumferential concave portion 82a, and the turn angle is set to be 30 degrees.

In addition, in the present embodiment, the shapes of the circumferential concave portion 82a and the stopper portion 85a are set such that the stopper portion 85a is disposed at the twelve o'clock position of the watch in the first restricting state, and the stopper portion 85a is disposed at the eleven o'clock position of the watch in the second restricting state.

In addition, in the papillotomy knife 80 of the present embodiment, a stabilizer 87 is provided to the outer sheath 81. The stabilizer 87 is a flat plate member having elastic force in view of insertability into the treatment instrument channel. As shown in FIGS. 21, 22, the stabilizer 87 is provided on the lower side of the outer sheath 81 in the drawings, thereby restricting the outer sheath 81 from bending in the lateral direction in FIG. 22, while allowing the outer sheath 81 to more easily bend in the upper direction in FIG. 22 since the stabilizer is located in the lower direction. That is, the stabilizer 87 is provided at a position on an outer circumferential surface side of the outer sheath 81, the position generally opposing to the knife portion 83c.

Figure 23:
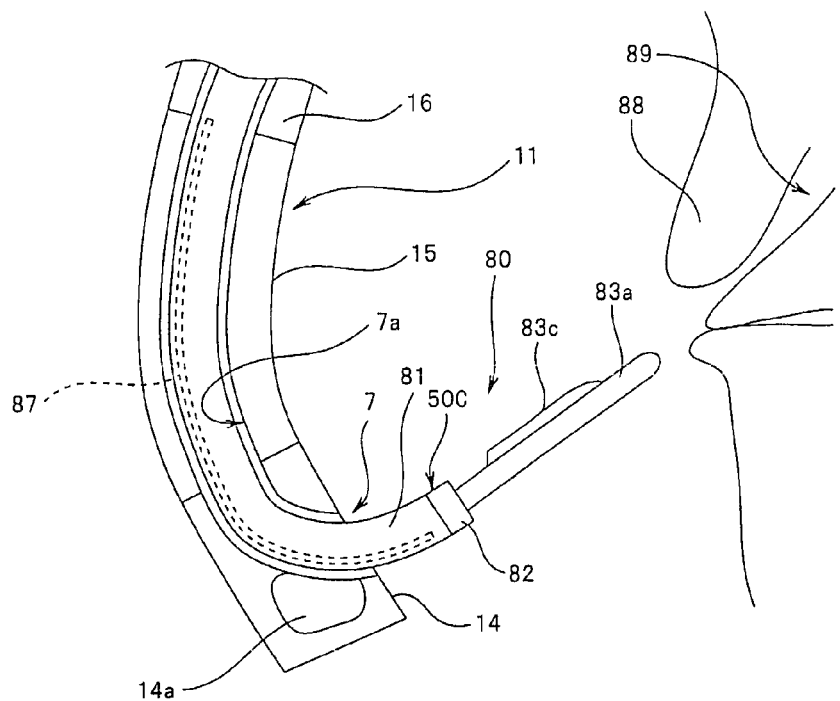
FIG. 23 is a view describing an operation of a stabilizer provided to the papillotomy knife.
Figure 24:
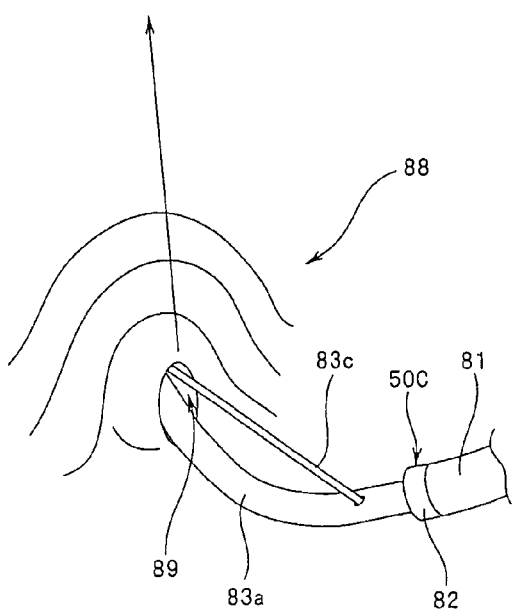
FIG. 24 is a view showing a state where an inner sheath of the papillotomy knife is inserted into a bile duct.

A length dimension of the stabilizer 87 is set such that a proximal end side of the stabilizer is disposed on a rear side of the bending portion 15 constituting the insertion portion 11 of the endoscope 2, as shown in FIG. 23. In addition, the stabilizer 87 is provided with a bending tendency. Specifically, the stabilizer 87 is bent such that the outside of the outer sheath 81 becomes convex shape as shown by the dashed lines in FIG. 23. Therefore, when the papillotomy knife 80 is inserted in the treatment instrument channel 7a of the insertion portion 11 bent as shown in FIG. 23, the stabilizer 87 is disposed on the outer circumferential side surface of the treatment instrument channel 7a where a bending radius is large. Then, when the dissection portion 33B is extracted into a body cavity from the treatment instrument channel 7a, the dissection portion 33B faces an upper part of a duodenal papilla.

Description will be made on an operation of the papillotomy knife 80 provided with the turn restricting mechanism portion 50C and the stabilizer 87 which are configured as described above.

Note that the endoscope used in the present embodiment is a side-view endoscope in which optical axes of an observation optical system and an illumination optical system are for example perpendicular to an axis in longitudinal direction of the insertion portion, but description will be made by adding the same reference numeral as that of the endoscope 2.

An operator inserts the papillotomy knife 80 into the treatment instrument channel 7a provided to the endoscope 2, in view of the disposing position of the stabilizer 87 provided to the outer sheath 81 of the papillotomy knife 80. At this time, the turn restricting mechanism portion 50C is in advance in the first restricting state shown in FIG. 22 in which the first contact surface 85b of the stopper portion 85a comes into contact with the first restricting surface 82b of the circumferential concave portion 82a.

Since the stabilizer 87 is provided to the outer sheath 81, the dissection portion 33B which passes through the treatment instrument channel 7a and is extracted from the treatment instrument extracting port 7 is extracted into the body cavity to face a duodenal papilla 88, as shown in FIG. 23.

Here, the operator inserts the inner sheath distal end 83a from the duodenal papilla 88 into a bile duct 89, while observing an endoscope screen. In the insertion state, as shown by the arrow in FIG. 24, the knife portion 83c faces in the twelve o'clock direction of the watch which is a generally upper direction in the drawing.

In dissection of the duodenal papilla, it is known that an ideal dissection can be performed when the knife portion 83c faces in the eleven o'clock direction of the watch. Therefore, the operator who uses the papillotomy knife 80 of the present embodiment performs an operation of changing the angle of the knife portion 83c facing in the twelve o'clock direction of the watch such that the knife portion 83c faces the eleven o'clock direction of the watch, in the insertion state shown in FIG. 24.

That is, the operator performs an operation of turning a guide member not shown to turn the inner sheath 83 with respect to the outer sheath 81. Then, similarly as in the above embodiments, a twisting force is gradually accumulated in the inner sheath 83, and when the twisting force accumulated in the inner sheath 83 exceeds a predetermined amount, the twisting force is released at once, thereby turning the inner sheath 83 and the dissection portion 33B.

Figure 26:
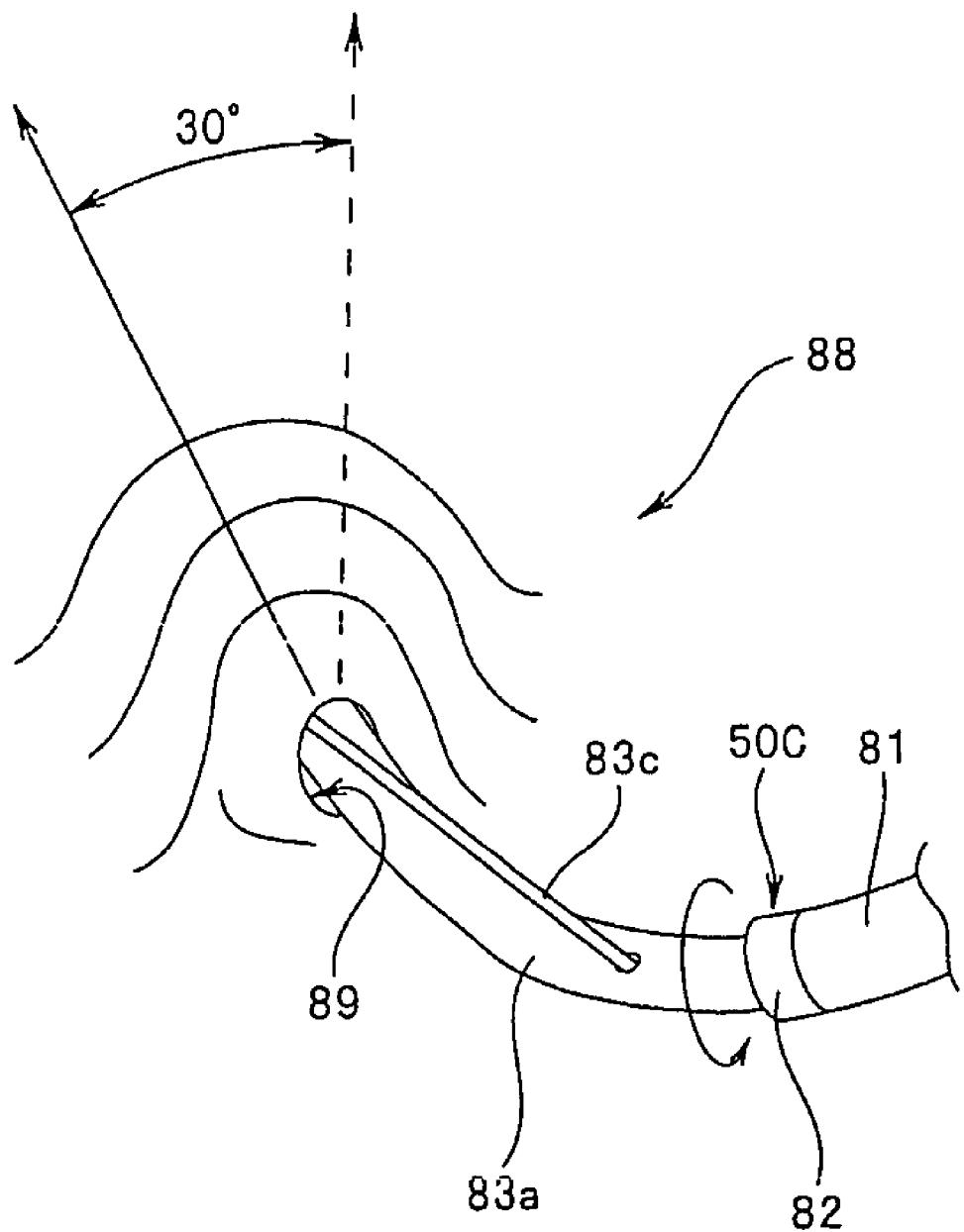
FIG. 26 is a view describing a state where a direction of a knife portion is changed from the twelve o'clock direction of a watch to the eleven o'clock direction of the watch while an inner sheath of the papillotomy knife being inserted in a bile duct.

Then, the stopper member 85 in the vicinity of the dissection portion 33B is also turned, and the turn restricting mechanism portion 50C in the first restricting state is changed to be in the second restricting state in which the second contact surface 85c of the stopper portion 85a comes into contact with the second restricting surface 82c of the circumferential concave portion 82a, as shown in FIG. 25. The change of the restricting state of the turn restricting mechanism portion 50C causes the dissection portion 33B to turn in the arrow direction as shown in FIG. 26, so that the direction of the knife portion 83c is changed from the twelve o'clock direction of the watch shown by the dashed lines to the eleven o'clock direction of the watch. In this state, the operator operates the slider to press the knife portion 83c against a living tissue, and dissects the living tissue by energizing a high frequency current to the conductive wire 84.

Thus, the stabilizer having a predetermined bending tendency is provided at a predetermined position of the outer sheath constituting the papillotomy knife. This allows the dissection portion to face the duodenal papilla in the desired direction when the dissection portion is extracted into the body cavity from the treatment instrument extracting port.

In addition, since the turn restricting mechanism portion is provided to the papillotomy knife extracted in the body cavity, in a case where the knife portion of the dissection portion is disposed facing in the twelve o'clock direction of the watch when the inner sheath is inserted into the bile duct in the first restricting state of the turn restricting mechanism portion, the operator performs a manual operation to turn the inner sheath and turns the dissection portion by the twisting force of the inner sheath. Then, with the turn of the dissection portion, the turn restricting mechanism portion is changed to the second restricting state, so that it is possible to change the direction of the knife portion facing in the twelve o'clock direction of the watch to face in the eleven o'clock direction.

In the embodiments described above, the medical device is described as the treatment instruments for endoscope such as the biopsy forceps 3, the grasping forceps 70, the papillotomy knife 80, and the like, but the medical device provided with the turn restricting mechanism portion is not limited to the treatment instrument for endoscope, and may be endoscope apparatuses 90, 90A configured as described below.

Description will be made on a fourth embodiment of the present invention referring to FIGS. 27 to 29.

Figure 27:
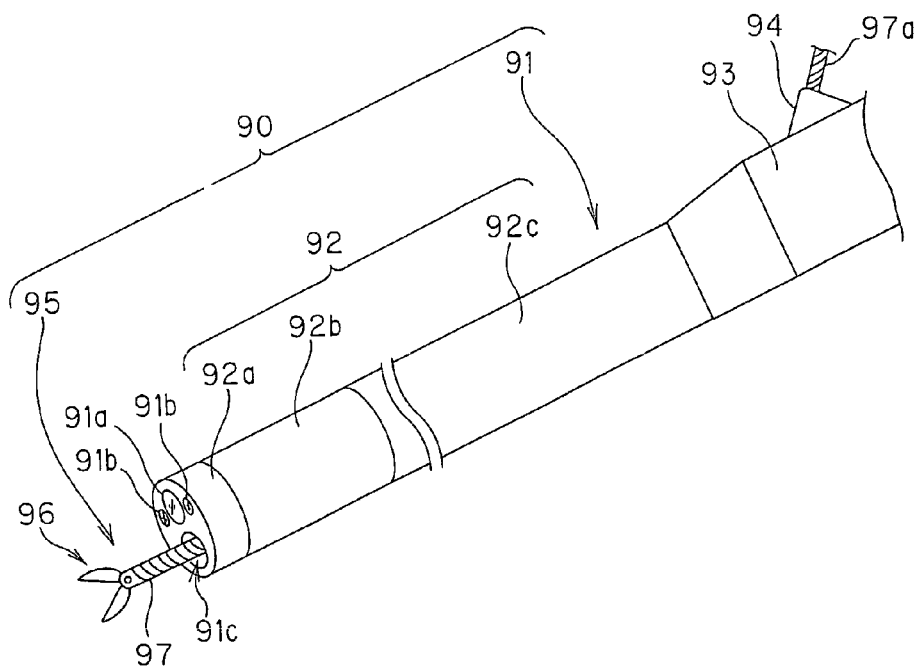
FIG. 27 is a view describing an endoscope apparatus provided with an endoscope and a treatment instrument for endoscope, as one example of the medical device.
Figure 28:
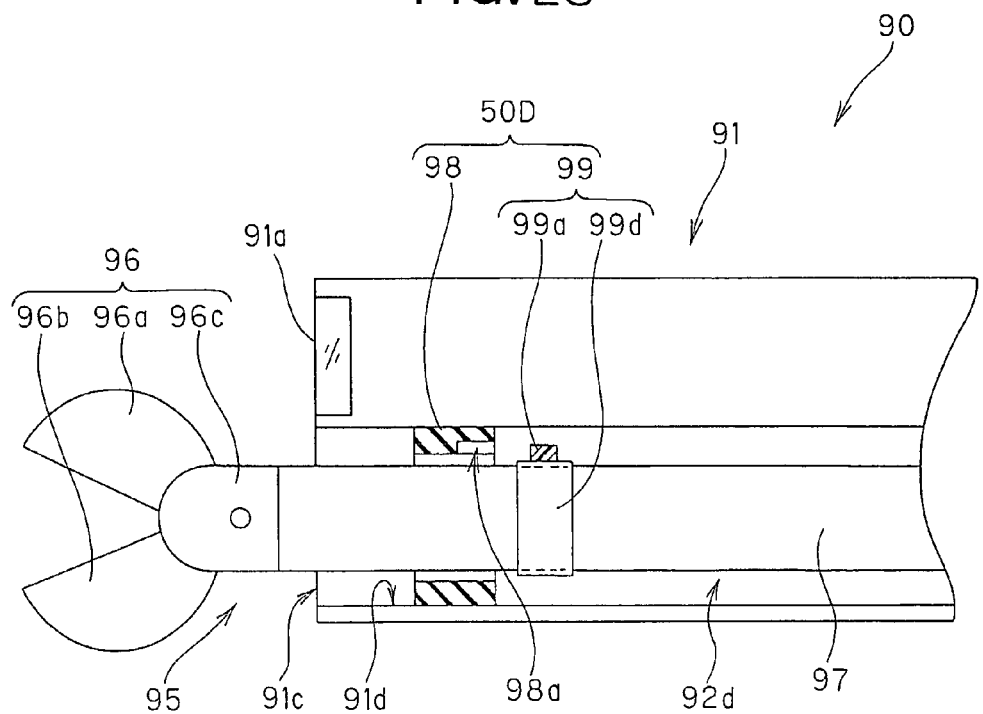
FIG. 28 is a view describing a turn restricting mechanism portion provided to an endoscope apparatus constituted by an endoscope and a treatment instrument for endoscope.

In the fourth embodiment, the medical device is the endoscope apparatus 90 provided with a turn restricting mechanism portion 50D as shown in FIGS. 27, 28. The endoscope apparatus 90 includes an endoscope 91 as an insertion portion, and a biopsy forceps 95 provided with a treatment portion 96 which is a function portion as well as a treatment instrument for endoscope and a coil sheath 97 which is a treatment instrument insertion portion as well as a turning force transmitting member. In the present embodiment, a direction of the treatment portion 96 of the biopsy forceps 95 can be changed by 90 degrees, for example, by turning operation of a sheath hand side 97a extending from a treatment instrument introducing port 94.

As shown in FIG. 27, the endoscope 91 includes an insertion portion 92, an operation portion 93, and the like. The insertion portion 92 includes in the following order from a distal end side thereof, a distal end portion 92a, a bending portion 92b, and a flexible tube portion 92c. The insertion portion 92 includes a treatment instrument channel (see the reference numeral 92d of FIG. 28) provided inside thereof. The distal end portion 92a includes on the distal end surface thereof an observation window 91a, an illumination window 91b, and a treatment instrument extracting port 91c which is a distal end opening of the treatment instrument channel 92d. The operation portion 93 is provided with the treatment instrument introducing port 94 communicating with the treatment instrument channel 92d.

On the other hand, the treatment portion 96 of the biopsy forceps 95 includes a pair of cups 96a, 96b, and a treatment portion base 96c, and the treatment portion 96 is so configured as to open and close by forward/backward movement of an operation wire not shown which is inserted in the coil sheath 97.

In the present embodiment, the turn restricting mechanism portion 50D includes a turn restricting member 98 and a stopper member 99. The turn restricting member 98 shown in FIG. 28 is made of an elastic member in an annular shape, for example, and is disposed in the treatment instrument channel 92d by press fitting, for example. As shown in FIG. 29, the turn restricting member 98 has a circumferential concave portion 98a formed therein, and a first restricting surface 98b and a second restricting surface 98c provided on the upper surface side in the drawing.

On the other hand, as shown in FIG. 28, the stopper member 99 includes a stopper portion 99a and a mounting member 99d, and the stopper portion 99a is integrally provided on an outer circumferential surface side of the mounting member 99d in a projecting manner. The stopper member 99 is integrally provided at a desired position of the coil sheath 97 by attaching the mounting member 99d to the coil sheath 97.

Figure 29:
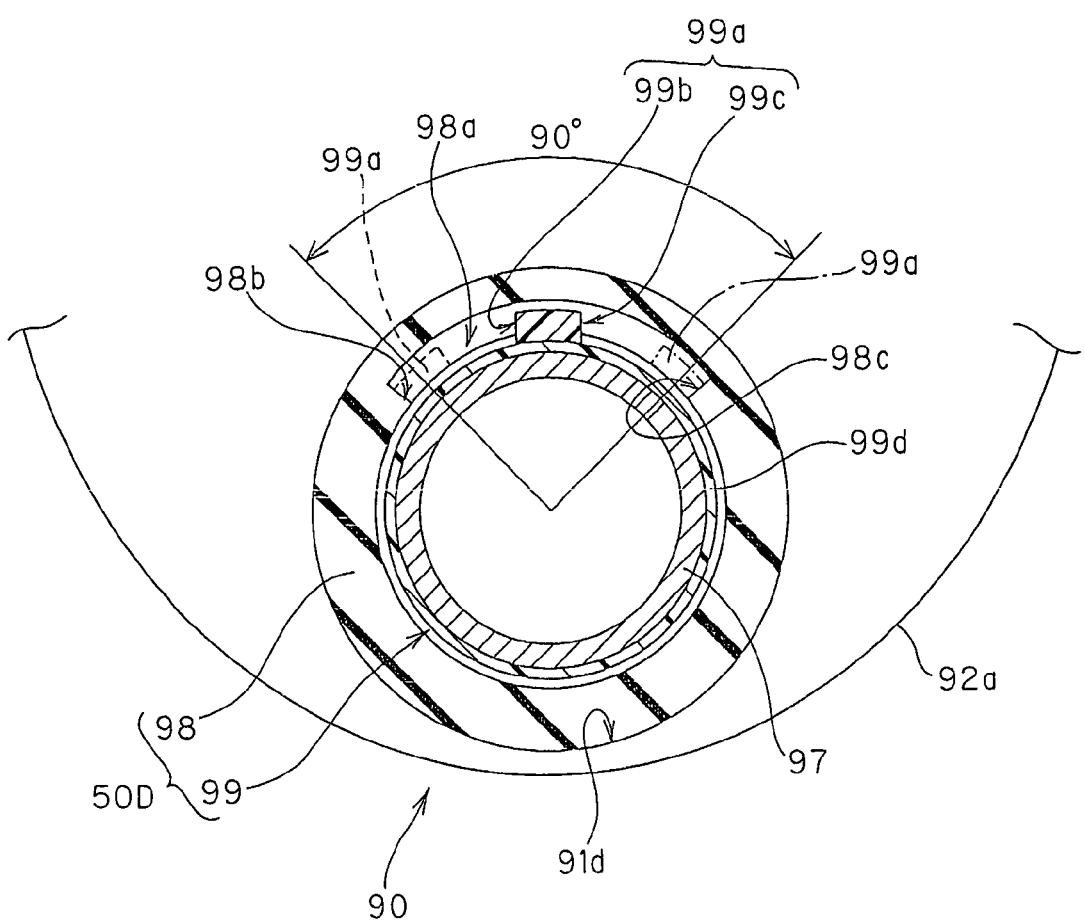
FIG. 29 is a view describing a relationship between a stopper member and a turn restricting member in the turn restricting mechanism portion.

As shown in FIG. 29, the stopper portion 99a includes a first contact surface 99b and a second contact surface 99c, and the stopper portion 99a of the stopper member 99 is disposed in the circumferential concave portion 98a of the turn restricting member 98. As a result, the turn restricting mechanism portion 50D is configured.

In the turn restricting mechanism portion 50D of the present embodiment, the stopper portion 99a is turnable from a position in a first restricting state in which the first contact surface 99b of the stopper portion 99a comes into contact with the first restricting surface 98b of the circumferential concave portion 98a as shown by the dashed lines in FIG. 29, to a position in a second restricting state in which the second contact surface 99c of the stopper portion 99a comes into contact with the second restricting surface 98c of the circumferential concave portion 98a as shown by the chain line. The turn angle is 90 degrees, for example.

Note that the turn angle can be set to a desired value by appropriately setting the length dimension in a circumferential direction of the circumferential concave portion 98a and the width dimension in a circumferential direction of the stopper portion 99a.

Description will be made on an operation of the endoscope apparatus 90 configured as described above.

First, an operator inserts in a body cavity the insertion portion 92 of the endoscope 91 in which the turn restricting member 98 is provided to the treatment instrument channel 92d. Then the operator performs an observation on an endoscope screen not shown.

When detecting a site to be inspected, the operator inserts the biopsy forceps 95 in the treatment instrument channel 92d via the treatment instrument introducing port 94. The stopper member 99 is provided at a desired position of the coil sheath 97 of the biopsy forceps 95, and the treatment portion 96 is introduced into the body cavity via the treatment instrument extracting port 91c by passing through an inner hole of the turn restricting member 98.

After that, the operator further performs an operation of advancing the treatment portion 96 toward deeper part in the body cavity, thereby allowing the stopper portion 99a to be disposed in the circumferential concave portion 98a or allowing the stopper portion 99a to come into contact with a proximal end surface of the turn restricting member 98. In a case where the stopper portion 99a comes into contact with the proximal end surface of the turn restricting member 98, the operator disposes the stopper portion 99a in the circumferential concave portion 98a by manual operation. As a result, the turn restricting mechanism portion 50D is configured in the endoscope apparatus 90.

Next, the operator performs an operation of turning the coil sheath 97 and sets the turn restricting mechanism portion 50D in the first restricting state, for example. In a case where the treatment portion 96 projected from a distal end surface of the endoscope 91 faces a site to be inspected not shown in a manner as shown in the above-described FIG. 8 in the first restricting state, for example, the operator moves the treatment portion 96 closer to the site to be inspected by the manual operation for advancing the insertion portion 92 of the endoscope 91 toward deeper part in the body cavity. Then after confirming that the site to be inspected has been disposed between the cups 96a, 96b in an open state, the operator collects the site to be inspected by performing an operation of closing the cups 96a, 96b.

On the other hand, when the turn restricting mechanism portion 50D is set in the first restricting state, in a case where the treatment portion 96 projected from the distal end surface of the endoscope 91 faces the site to be inspected not shown in a manner as shown in above-described FIG. 9, the operator performs an operation of turning the sheath hand side 97a in a predetermined direction in order to change the direction of the treatment portion 96 by 90 degrees. Then, the coil sheath 97 is gradually twisted, and the twisting force is accumulated in the coil sheath 97. When the twisting force accumulated in the coil sheath 97 exceeds a predetermined amount, the twisting force accumulated in the coil sheath 97 is released at once. That is, by turning the treatment portion 96, the turn restricting mechanism portion 50D in the first restricting state is changed to be in the second restricting state in which the second contact surface 99c of the stopper portion, 99a comes into contact with the second restricting surface 98c of the circumferential concave portion 98a. At this time, the direction of the treatment portion 96 with respect to the site to be inspected is changed to be the positional relationship shown in FIG. 8.

Thus, the turn restricting member is provided in the treatment instrument channel of the endoscope, and the stopper member is provided at the predetermined position of the treatment instrument for endoscope inserted in the treatment instrument channel, so that the turn restricting mechanism portion is configured in a state where the treatment instrument for endoscope is inserted in the treatment instrument channel of the endoscope. With this configuration, when the treatment portion of the treatment instrument for endoscope is turned with respect to the treatment instrument channel of the endoscope, it is possible to change the direction of the treatment portion between the positions in the first restricting state and the second restricting state, in which the direction of the treatment portion is restricted by the turn restricting mechanism portion.

Note that the turn restricting member may be configured to be detachably attached to or integrally fixed to the treatment instrument channel. In addition, also the stopper member may be configured to be detachably attached or integrally fixed to the coil sheath of the treatment instrument for endoscope.

Figure 30:
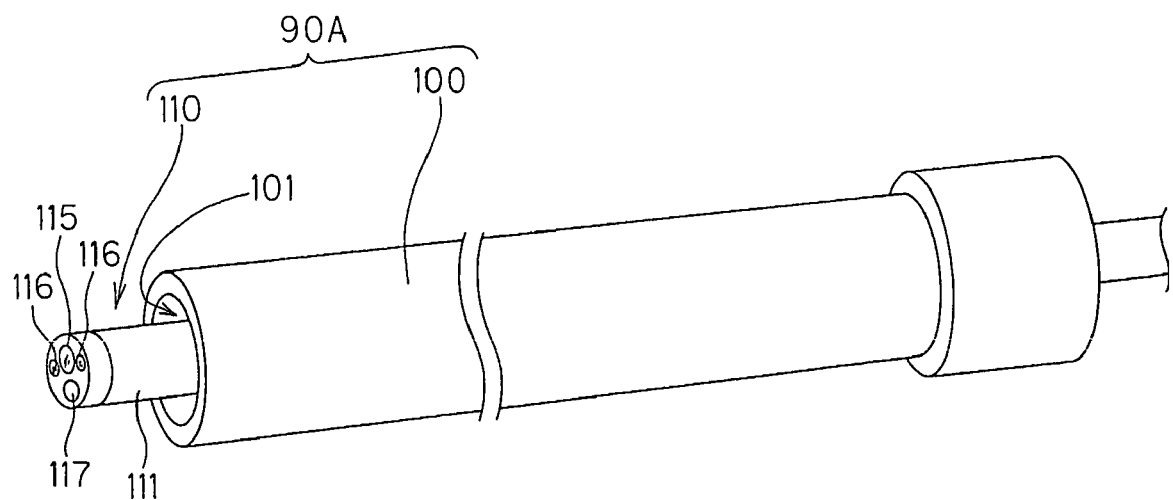
FIG. 30 is a view describing an endoscope apparatus provided with an endoscopic overtube and an endoscope, as one example of the medical device.
Figure 31:
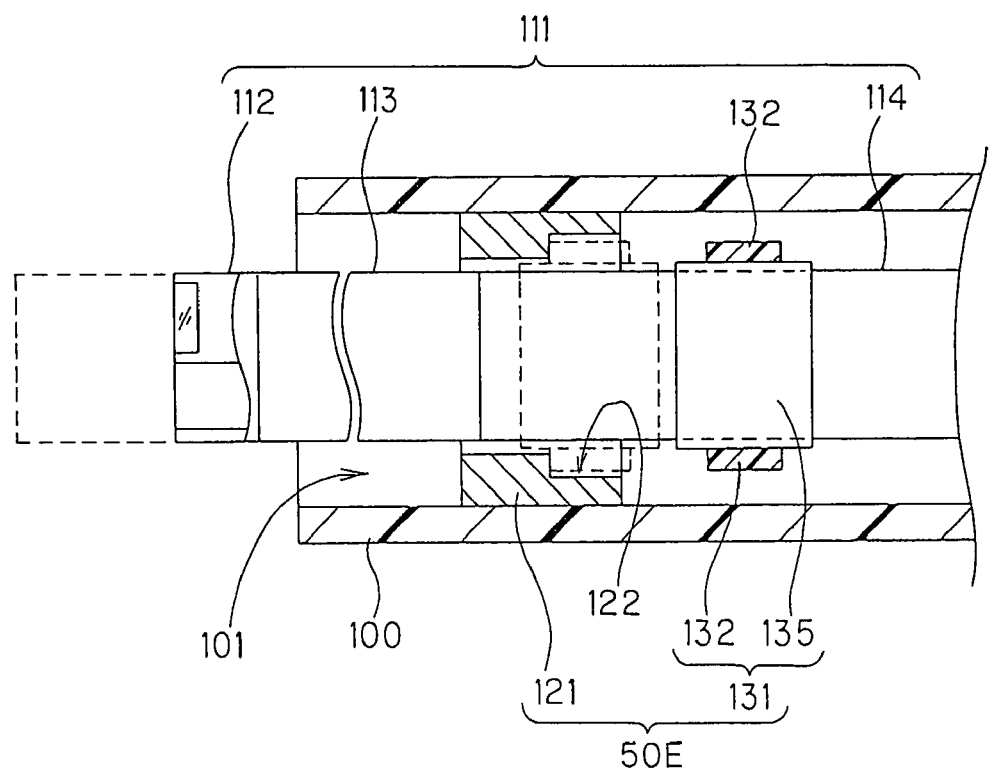
FIG. 31 is a view describing the turn restricting mechanism portion provided to the endoscope apparatus constituted by the endoscopic overtube and the endoscope.
Figure 32:
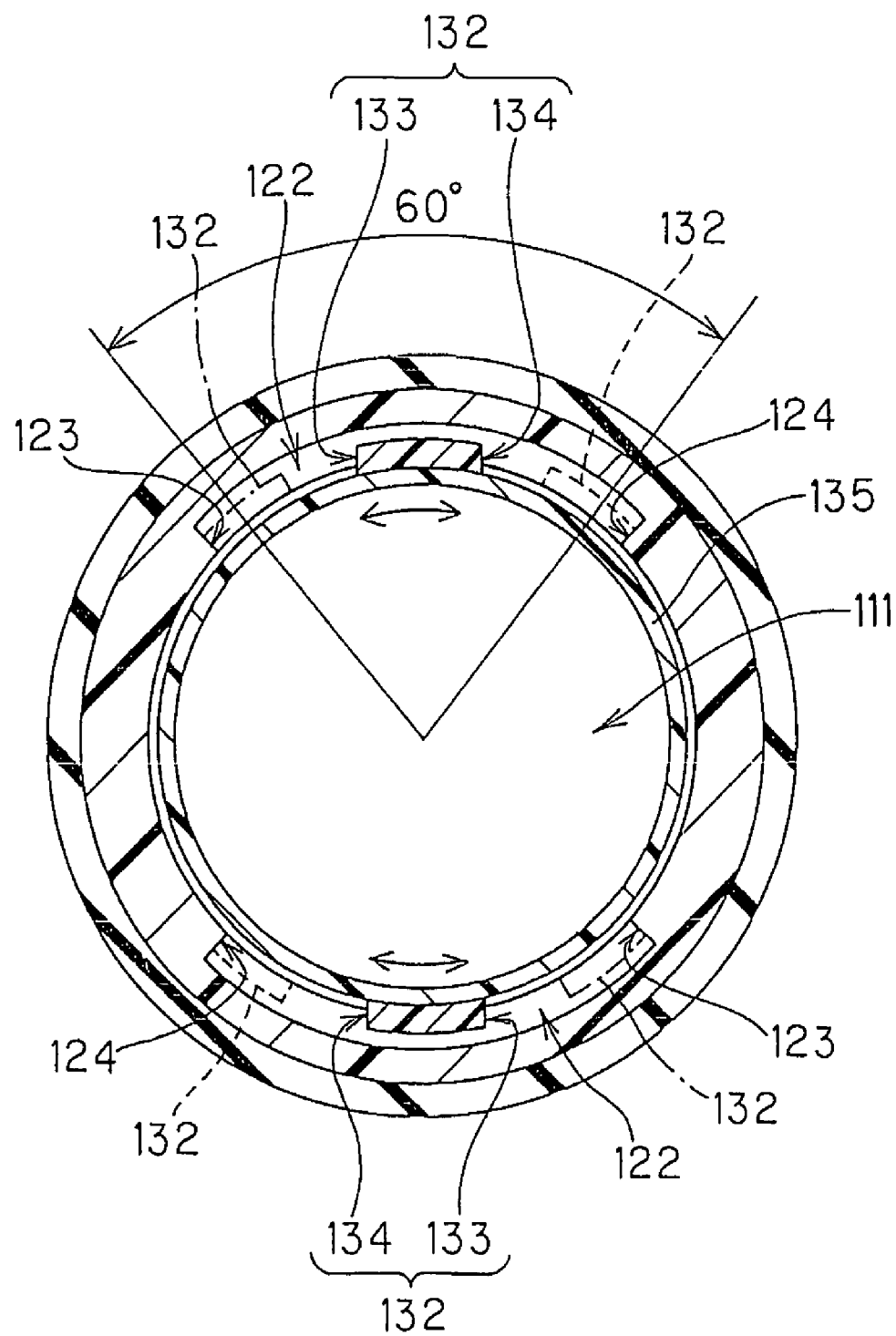
FIG. 32 is a view describing a relationship between the stopper member and the turn restricting member in the turn restricting mechanism portion.

Furthermore, though the endoscope apparatus 90 provided with the turn restricting mechanism portion 50D is constituted by the endoscope 91 and the treatment instrument for endoscope such as the biopsy forceps 95 and the like in the present embodiment, the medical device may be an endoscope apparatus 90A shown in FIGS. 30 to 32.

Description will be made on the endoscope apparatus 90A referring to FIGS. 30 to 32.

As shown in FIG. 30, the endoscope apparatus 90A includes an endoscopic overtube (hereinafter abbreviated as an overtube) 100, and an endoscope 110 provided with an observation optical system as a function portion and a flexible endoscope insertion portion 111 as a turning force transmitting member.

The overtube 100 of the present invention is a flexible tube body including an endoscope insertion hole 101 through which the endoscope insertion portion 111 of the endoscope 110 is insertable. Meanwhile, the endoscope 110 includes the endoscope insertion portion 111, an operation portion not shown, and the like. The endoscope insertion portion 111 includes in the following order from a distal end side thereof, a distal end portion 112, a bending portion 113, and a flexible tube portion 114. The endoscope insertion portion 111 includes on the distal end surface thereof an observation window 115 constituting the observation optical system which is the function portion, an illumination window 116, and a treatment instrument extracting port 117 which is a distal end opening of the treatment instrument channel.

In the present embodiment, a turn restricting mechanism portion 50E includes a turn restricting member 121 and a stopper member 131. The turn restricting member 121 shown in FIG. 31 is formed in an annular shape by a rigid member, for example, and integrally fixed at a predetermined position of the endoscope insertion hole 101 in the overtube 100. The turn restricting member 121 has a pair of circumferential concave portions 122 formed in an opposing positional relationship, and each of the circumferential concave portions 122 is provided on the upper surface side and the lower surface side in the drawing, respectively, as shown in FIG. 32. Each of the circumferential concave portions 122 includes a first restricting surface 123 and a second restricting surface 124.

On the other hand, the stopper member 131 includes a pair of stopper portions 132 and a mounting member 135 as shown in FIG. 31, and the stopper portions 132 are provided in a projecting and integral manner on an outer circumferential surface side of the mounting member 135 in an opposing positional relationship. The stopper member 131 is integrally provided at a desired position of the flexible tube portion 114 by attaching the mounting member 135, for example, to the flexible tube portion 114 of the endoscope insertion portion 111. Each of the stopper portions 132 includes a first contact surface 133 and a second contact surface 134 as shown in FIG. 32, and the stopper portions 132 of the stopper member 131 are disposed in the circumferential concave portions 122 of the turn restricting member 121. As a result, the turn restricting mechanism portion 50E is configured.

In the turn restricting mechanism portion 50E of the present embodiment, as shown in FIG. 32, the stopper portions 132 are turnable from a position in a first restricting state in which the first contact surfaces 133 of the stopper portions 132 and the first restricting surfaces 123 of the circumferential concave portions 122 come into contact with each other to a position in a second restricting state in which the second contact surfaces 134 of the stopper portions 132 and the second restricting surfaces 124 of the circumferential concave portions 122 come into contact with each other. The turn angle is 60 degrees, for example.

Note that the turn angle can be set to a desired value by appropriately setting the length dimension in a circumferential direction of the circumferential concave portions 122 and the width dimension in a circumferential direction of the stopper portions 132.

Description will be made on an operation of the endoscope apparatus 90A configured as described above.

First, in order to insert the endoscope insertion portion 111 of the endoscope 110 into a body cavity, an operator secures in advance an insertion path for the endoscope insertion portion 111 by disposing in the body cavity the overtube 100 in which the turn restricting member 121 is provided in the endoscope insertion hole 101.

Next, the operator inserts into the endoscope insertion hole 101 in the overtube 100 the endoscope insertion portion 111 including the stopper member 131 mounted, for example, at a distal end side of the flexible tube portion 114. Then, the endoscope insertion portion 111 smoothly advances toward a deep direction in the endoscope insertion hole 101.

Then, the operator continues the operation of advancing the endoscope insertion portion 111, and thereby the distal end portion 112 passes through an inner hole of the turn restricting member 121 to be extracted into the body cavity from a distal end surface of the overtube 100. After that, the operator further performs an operation of advancing the endoscope insertion portion 111 toward the deeper part in the body cavity, thereby allowing the stopper portions 132 to be disposed in the circumferential concave portions 122 or allowing the stopper portions 132 to come into contact with a proximal end surface of the turn restricting member 121. In a case where the stopper portions 132 come into contact with the proximal end surface of the turn restricting member 121, the operator disposes the stopper portions 132 in the circumferential concave portions 122 by manual operation. As a result, the turn restricting mechanism portion 50E is configured in the endoscope apparatus 90A.

Next, the operator turns the endoscope insertion portion 111 extended from the proximal end surface of the overtube 100, and sets the turn restricting mechanism portion 50E in a first restricting state, for example. Then, in the first restricting state, the operator observes on an endoscope screen not shown an endoscope image of a site to be observed which is captured by the observation optical system of the endoscope 110. At this time, if the operator would like to observe the site to be observed by changing the position of the observation optical system by 60 degrees, the operator performs an operation of twisting the endoscope insertion portion 111.

Then, the endoscope insertion portion 111 is turned, and the turn restricting mechanism portion 50E in the first restricting state is changed to be in a second restricting state in which the second contact surfaces 134 of the stopper portions 132 and the second restricting surfaces 124 of the circumferential concave portions 122 come into contact with each other, and thereby the endoscope image observed through the observation window 115 is changed. That is, it is possible to appropriately change an angle of view of the endoscope image displayed on the endoscope screen not shown.

Thus, the turn restricting member is provided in the endoscope insertion hole in the overtube, and the stopper member is provided at the predetermined position of the endoscope insertion portion inserted in the endoscope insertion hole, so that the turn restricting mechanism portion is configured in the state where the endoscope insertion portion is inserted in the endoscope insertion hole in the overtube, and it is possible to perform an observation, treatment, or the like by changing the position of the observation optical system provided to the endoscope between the position in the first restricting state and the position in the second restricting state.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical device comprising:
   a tubular insertion portion;
   a function portion disposed closer to a distal end side than a distal end surface of the insertion portion;
   a turning force transmitting member for turning the function portion by a turning operation, the turning force transmitting member being inserted in the insertion portion and turnable in a circumferential direction in the insertion portion;
   an operation portion to be operated to turn the turning force transmitting member; and
   a turn restricting mechanism portion for restricting a turn position of the function portion turned by a turning force transmitted by the turning force transmitting member with respect to the insertion portion at a first turn-restricting position and at a second turn-restricting position turned by a predetermined angle from the first turn-restricting position,
   wherein the turn restricting mechanism portion includes:
   a turn restricting member integrally provided to the insertion portion and having a restricting surface in a circumferential direction;
   a stopper member provided near the function portion or to the turning force transmitting member, the stopper member including a contact surface which is contactable to and separatable from a restricting surface of the turn restricting member; and
   a stopper turning space which allows the stopper member to turn about an axis direction, the stopper member being formed in a circumferential direction about the axis direction, and
   wherein the turn restricting mechanism portion further includes a state where turning of the function portion with respect to the insertion portion is restricted at the first turn-restricting position or the second turn-restricting position by contact between the restricting surface and the contact surface, and a state where the function portion is turnable with respect to the insertion portion by separating the restricting surface and the contact surface in the circumferential direction in the stopper turning space.

2. The medical device according to claim 1, wherein the turn restricting member and the stopper member each has a partial cylinder shape, and the restricting surface and the contact surface are planes parallel to the longitudinal axis.

3. A treatment instrument for endoscope, comprising:
   a tubular insertion portion introduced in a body cavity through a treatment instrument channel provided to an endoscope insertion portion;
   a treatment portion for performing a treatment in the body cavity, the treatment portion being disposed closer to a distal end side than a distal end surface of the insertion portion;
   a turning force transmitting member for transmitting a turning force to turn the treatment portion in a circumferential direction, the turning force transmitting member being inserted in the tubular insertion portion in a forwardly/backwardly movable manner and being turned in the circumferential direction;
   an operation portion to be operated to turn the turning force transmitting member; and
   a turn restricting mechanism portion for restricting a turn position of the treatment portion turned by the turning force transmitted by the turning force transmitting member with respect to the insertion portion at a first turn-restricting position and at a second turn-restricting position turned by a predetermined angle from the first turn-restricting position,
   wherein the turn restricting mechanism portion includes:
   a turn restricting member integrally provided to the insertion portion and having a restricting surface in a circumferential direction;
   a stopper member including a contact surface which is contactable to and separatable from a restricting surface of the turn restricting member; and
   a stopper turning space which allows the stopper member to turn about an axis direction, the stopper turning space being formed in a circumferential direction about the axis direction, and
   wherein the turn restricting mechanism portion further includes a state where turning of the treatment portion with respect to the insertion portion is restricted at the first turn-restricting position or the second turn-restricting position by contact between the restricting surface and the contact surface, and a state where the treatment portion is turnable with respect to the insertion portion by separating the restricting surface and the contact surface in the circumferential direction in the stopper turning space.

4. The treatment instrument for endoscope according to claim 3, further comprising a connecting member for connecting the treatment portion and the turn restricting mechanism portion.

5. The treatment instrument for endoscope according to claim 3, wherein the turn restricting mechanism portion further comprises:
   a joining member for turnably holding the stopper member with respect to the turn restricting member and for preventing the stopper member from falling off from the turn restricting member, wherein the contact surface stops the treatment portion turned by the turning force transmitted by the turning force transmitting member at the first turn-restricting position or the second turn-restricting position.

6. The treatment instrument for endoscope according to claim 5, wherein a turn angle from the first turn-restricting position to the second turn-restricting position which are restricted by the turn restricting mechanism portion is less than 180 degrees.

7. The treatment instrument for endoscope according to claim 3, wherein the treatment portion includes a pair of biopsy cups in an openable/closable manner.

8. The treatment instrument for endoscope according to claim 4, wherein the treatment portion includes a pair of biopsy cups in an openable/closable manner.

9. The treatment instrument for endoscope according to claim 3, wherein the treatment portion includes a pair of forceps pieces in a turnable manner.

10. The treatment instrument for endoscope according to claim 3, wherein the treatment portion is a knife portion including a conductive wire capable of carrying a high frequency current.

11. An endoscope apparatus comprising:
an endoscope including a treatment instrument channel in an endoscope insertion portion constituting an insertion portion;
a treatment instrument for endoscope, including:
a treatment portion for performing a treatment in a body cavity, the treatment portion being disposed closer to a distal end side than a treatment instrument extracting port of the endoscope insertion portion; and
a treatment instrument insertion portion for transmitting a turning force for turning the treatment portion in a circumferential direction, the treatment instrument insertion portion being inserted in the treatment instrument channel and being turned in the circumferential direction;
an operation portion to be operated to turn the turning force transmitting member; and
a turn restricting mechanism portion for restricting a turn position of the treatment portion with respect to the endoscope at a first turn-restricting position and at a second turn-restricting position turned by a predetermined angle from the first turn-restricting position,
wherein the turn restricting mechanism portion includes:
a turn restricting member which is disposed to the treatment instrument channel of the endoscope and has a restricting surface in a circumferential direction;
a stopper member which is provided to the treatment instrument insertion portion of the treatment instrument for endoscope, the stopper member including a contact surface which is contactable to and separatable from a restricting surface of the turn restricting member; and
a stopper turning space which allows the stopper member to turn about an axis direction, the stopper turning space being formed in a circumferential direction about the axis direction, and
wherein the turn restricting mechanism portion further includes a state where turning of the treatment portion with respect to the treatment instrument channel is restricted at the first turn-restricting position or the second turn-restricting position by contact between the restricting surface and the contact surface, and a state where the treatment portion is turnable with respect to the treatment instrument channel by separating the restricting surface and the contact surface in the circumferential direction in the stopper turning space.

12. The endoscope apparatus according to claim 11, wherein
the contact surface stops the treatment portion turned by a turning force transmitted by the treatment instrument insertion portion at a first turn-restricting position or at a second turn-restricting position.

13. An endoscope apparatus comprising:
an endoscopic overtube disposed by being inserted in a body cavity;
an endoscope including:
a function portion for performing an observation in the body cavity, the function portion being disposed closer to a distal end side than a distal end surface of the endoscopic overtube; and
an endoscope insertion portion for transmitting a turning force to turn the function portion in a circumferential direction, the endoscope insertion portion being inserted in an endoscope insertion hole and turned in the circumferential direction;
an operation portion to be operated to turn the turning force transmitting member; and
a turn restricting mechanism portion for restricting a turn position of the function portion with respect to the endoscopic overtube at a first turn-restricting position and at a second turn-restricting position turned by a predetermined angle from the first turn-restricting position
wherein the turn restricting mechanism portion includes:
a turn restricting member disposed to the endoscope insertion hole of the overtube and having a restricting surface in a circumferential direction;
a stopper member provided to the endoscope insertion portion and including a contact surface which is contactable to and separatable from a restricting surface of the turn restricting member; and
a stopper turning space which allows the stopper member to turn about an axis direction, the stopper turning space being formed in a circumferential direction about the axis direction, and
wherein the turn restricting mechanism portion further includes a state where turning of the function portion with respect to the endoscope insertion hole is restricted at the first turn-restricting position or the second turn-restricting position by contact between the restricting surface and the contact surface, and a state where the function portion is turnable with respect to the endoscope insertion hole by separating the restricting surface and the contact surface in the circumferential direction in the stopper turning apace.

14. The endoscope apparatus according to claim 13, wherein
the contact surface stops the function portion turned by the turning force transmitted by the endoscope insertion portion at a first turn-restricting position or at a second turn-restricting position.

15. The endoscope apparatus according to claim 3, wherein
the turn restricting member and the stopper member each have a partial cylinder shape; and
the restricting surface and the contact surface are planes parallel to the longitudinal axis.

16. The endoscope apparatus according to claim 11, wherein
the turn restricting member and the stopper member each have a partial cylinder shape, and
the restricting surface and the contact surface are planes parallel to the longitudinal axis.

17. The endoscope apparatus according to claim 13, wherein
the turn restricting member and the stopper member each have a partial cylinder shape, and
the restricting surface and the contact surface are planes parallel to the longitudinal axis.

* * * * *